(12) United States Patent
Abunassar et al.

(10) Patent No.: US 11,660,189 B2
(45) Date of Patent: May 30, 2023

(54) WIDE CLIP WITH NONDEFORMABLE WINGS

(71) Applicant: EVALVE, INC., Santa Clara, CA (US)

(72) Inventors: Chad Abunassar, San Francisco, CA (US); Jessie Garcia, Newark, CA (US); Gabriel Gonzales, Milpitas, CA (US); Samir Jain, Mountain View, CA (US); Casey Barbarino, San Francisco, CA (US); Santosh Prabhu, Sunnyvale, CA (US)

(73) Assignee: EVALVE, INC., Santa Clara, CA (US)

( * ) Notice: Subject to any disclaimer, the term of this patent is extended or adjusted under 35 U.S.C. 154(b) by 371 days.

(21) Appl. No.: 16/928,599

(22) Filed: Jul. 14, 2020

(65) Prior Publication Data

US 2021/0015607 A1 Jan. 21, 2021

Related U.S. Application Data

(60) Provisional application No. 62/874,342, filed on Jul. 15, 2019.

(51) Int. Cl.
*A61F 2/24* (2006.01)

(52) U.S. Cl.
CPC ...... *A61F 2/246* (2013.01); *A61F 2220/0008* (2013.01); *A61F 2230/0093* (2013.01); *A61F 2250/0036* (2013.01); *A61F 2250/0037* (2013.01)

(58) Field of Classification Search
CPC ..... A61F 2/246; A61F 2220/0008; A61F 2/24
See application file for complete search history.

(56) References Cited

U.S. PATENT DOCUMENTS

| | | | |
|---|---|---|---|
| 3,378,010 A | 4/1968 | Codling et al. |
| 3,874,388 A | 4/1975 | King et al. |
| 4,007,743 A | 2/1977 | Blake |
| 4,055,861 A | 11/1977 | Carpentier et al. |
| 4,327,736 A | 5/1982 | Inoue |

(Continued)

FOREIGN PATENT DOCUMENTS

| | | |
|---|---|---|
| CA | 2 296 317 C | 1/2009 |
| EP | 0 558 031 B1 | 9/1993 |

(Continued)

*Primary Examiner* — Julian W Woo
(74) *Attorney, Agent, or Firm* — Baker Botts L.L.P.

(57) ABSTRACT

Fixation device for fixation of leaflets of a heart valve includes a central assembly and at least one arm moveably coupled to the central assembly. The at least one arm includes a body portion having a first end and a second end and a longitudinal axis defined therebetween, the second end being moveable between a closed position and an open position, the body portion having opposing body lateral sides, each body lateral side extending between the first end and the second end, the body portion having a body portion width defined between the opposing body lateral sides. The at least one arm further includes first and second nondeformable wing extensions, each wing extension extending laterally from a respective lateral side, each wing extension having a lateral outer edge, wherein a maximum arm width is defined between the outer lateral edge of the first wing extension and the outer lateral edge of the second wing extension. The fixation device further includes at least one gripping element moveable relative to the at least one arm to capture a native leaflet therebetween.

44 Claims, 22 Drawing Sheets

(56) References Cited

U.S. PATENT DOCUMENTS

| | | | |
|---|---|---|---|
| 4,340,091 | A | 7/1982 | Skelton et al. |
| 4,657,024 | A | 4/1987 | Coneys |
| 4,693,248 | A | 9/1987 | Failla |
| 4,716,886 | A | 1/1988 | Schulman et al. |
| 4,795,458 | A | 1/1989 | Regan |
| 4,809,695 | A | 3/1989 | Gwathmey et al. |
| 4,930,674 | A | 6/1990 | Barak |
| 5,002,562 | A | 3/1991 | Oberlander |
| 5,069,679 | A | 12/1991 | Taheri |
| 5,098,440 | A | 3/1992 | Stead |
| 5,125,895 | A | 6/1992 | Buchbinder et al. |
| 5,147,370 | A | 9/1992 | McNamara et al. |
| 5,171,259 | A | 12/1992 | Inoue |
| 5,222,963 | A | 6/1993 | Brinkerhoff et al. |
| 5,271,544 | A | 12/1993 | Fox et al. |
| 5,327,905 | A | 7/1994 | Avitall |
| 5,330,501 | A | 7/1994 | Tovey et al. |
| 5,334,217 | A | 8/1994 | Das |
| 5,363,861 | A | 11/1994 | Edwards et al. |
| 5,389,077 | A | 2/1995 | Melinyshyn et al. |
| 5,403,326 | A | 4/1995 | Harrison et al. |
| 5,425,744 | A | 6/1995 | Fagan et al. |
| 5,450,860 | A | 9/1995 | O'Connor |
| 5,452,837 | A | 9/1995 | Williamson, IV et al. |
| 5,456,400 | A | 10/1995 | Shichman et al. |
| 5,456,674 | A | 10/1995 | Bos et al. |
| 5,478,353 | A | 12/1995 | Yoon |
| 5,542,949 | A | 8/1996 | Yoon |
| 5,562,678 | A | 10/1996 | Booker |
| 5,601,224 | A | 2/1997 | Bishop et al. |
| 5,601,574 | A | 2/1997 | Stefanchik et al. |
| 5,607,462 | A | 3/1997 | Imran |
| 5,607,471 | A | 3/1997 | Seguin et al. |
| 5,609,598 | A | 3/1997 | Laufer et al. |
| 5,611,794 | A | 3/1997 | Sauer et al. |
| 5,636,634 | A | 6/1997 | Kordis et al. |
| 5,695,504 | A | 12/1997 | Gifford, III et al. |
| 5,713,911 | A | 2/1998 | Racenet et al. |
| 5,716,417 | A | 2/1998 | Girard et al. |
| 5,741,297 | A | 4/1998 | Simon |
| 5,755,778 | A | 5/1998 | Kleshinski |
| 5,782,239 | A | 7/1998 | Webster, Jr. |
| 5,797,960 | A | 8/1998 | Stevens et al. |
| 5,810,847 | A | 9/1998 | Laufer et al. |
| 5,814,097 | A | 9/1998 | Sterman et al. |
| 5,843,178 | A | 12/1998 | Vanney et al. |
| 5,849,019 | A | 12/1998 | Yoon |
| 5,855,601 | A | 1/1999 | Bessler et al. |
| 5,976,159 | A | 11/1999 | Bolduc et al. |
| 6,015,417 | A | 1/2000 | Reynolds, Jr. |
| 6,048,351 | A | 4/2000 | Gordon et al. |
| 6,079,414 | A | 6/2000 | Roth |
| 6,117,144 | A | 9/2000 | Nobles et al. |
| 6,120,496 | A | 9/2000 | Whayne et al. |
| 6,149,658 | A | 11/2000 | Gardiner et al. |
| 6,165,183 | A | 12/2000 | Kuehn et al. |
| 6,182,664 | B1 | 2/2001 | Cosgrove |
| 6,193,734 | B1 | 2/2001 | Bolduc et al. |
| 6,200,315 | B1 | 3/2001 | Gaiser et al. |
| 6,217,528 | B1 | 4/2001 | Koblish et al. |
| 6,269,819 | B1 | 8/2001 | Oz et al. |
| 6,290,674 | B1 | 9/2001 | Roue et al. |
| 6,312,447 | B1 | 11/2001 | Grimes |
| 6,332,880 | B1 | 12/2001 | Yang et al. |
| 6,346,074 | B1 | 2/2002 | Roth |
| 6,419,696 | B1 | 7/2002 | Ortiz et al. |
| 6,461,366 | B1 | 10/2002 | Seguin |
| 6,482,224 | B1 | 11/2002 | Michler et al. |
| 6,496,420 | B2 | 12/2002 | Manning |
| 6,544,215 | B1 | 4/2003 | Bencini et al. |
| 6,551,303 | B1 | 4/2003 | Van Tassel et al. |
| 6,575,971 | B2 | 6/2003 | Hauck et al. |
| 6,599,311 | B1 | 7/2003 | Biggs et al. |
| 6,626,930 | B1 | 9/2003 | Allen et al. |
| 6,629,534 | B1 | 10/2003 | St. Goar et al. |
| 6,669,687 | B1 | 12/2003 | Saadat |
| 6,695,866 | B1 | 2/2004 | Kuehn et al. |
| 6,719,767 | B1 | 4/2004 | Kimblad |
| 6,752,813 | B2 | 6/2004 | Goldfarb et al. |
| 6,770,083 | B2 | 8/2004 | Seguin |
| 6,797,002 | B2 | 9/2004 | Spence et al. |
| 6,837,867 | B2 | 1/2005 | Kortelling |
| 6,855,137 | B2 | 2/2005 | Bon |
| 6,875,224 | B2 | 4/2005 | Grimes |
| 6,908,481 | B2 | 6/2005 | Cribier |
| 6,926,730 | B1 | 8/2005 | Nguyen et al. |
| 7,011,669 | B2 | 3/2006 | Kimblad |
| 7,101,395 | B2 | 9/2006 | Tremulis et al. |
| 7,112,207 | B2 | 9/2006 | Allen et al. |
| 7,125,421 | B2 | 10/2006 | Tremulis et al. |
| 7,226,467 | B2 | 6/2007 | Lucatero et al. |
| 7,556,632 | B2 | 7/2009 | Zadno |
| 7,563,267 | B2 | 7/2009 | Goldfarb et al. |
| 7,569,062 | B1 | 8/2009 | Kuehn et al. |
| 7,604,646 | B2 | 10/2009 | Goldfarb et al. |
| 7,635,329 | B2 | 12/2009 | Goldfarb et al. |
| 7,655,015 | B2 | 2/2010 | Goldfarb et al. |
| 7,666,204 | B2 | 2/2010 | Thornton et al. |
| 7,736,388 | B2 | 6/2010 | Goldfarb et al. |
| 7,811,296 | B2 | 10/2010 | Goldfarb et al. |
| 7,972,323 | B1 | 7/2011 | Bencini et al. |
| 7,981,139 | B2 | 7/2011 | Martin et al. |
| 8,057,493 | B2 | 11/2011 | Goldfarb et al. |
| 8,062,313 | B2 | 11/2011 | Kimblad |
| 8,118,822 | B2 | 2/2012 | Schaller et al. |
| 8,216,230 | B2 | 7/2012 | Hauck et al. |
| 8,216,256 | B2 | 7/2012 | Raschdorf, Jr. et al. |
| 8,303,608 | B2 | 11/2012 | Goldfarb et al. |
| 8,500,761 | B2 | 8/2013 | Goldfarb et al. |
| 8,734,505 | B2 | 5/2014 | Goldfarb et al. |
| 8,740,920 | B2 | 6/2014 | Goldfarb et al. |
| 9,510,829 | B2 | 12/2016 | Goldfarb et al. |
| 10,076,415 | B1 | 9/2018 | Metchik et al. |
| 10,105,222 | B1 | 10/2018 | Metchik et al. |
| 10,123,873 | B1 | 11/2018 | Metchik et al. |
| 10,130,475 | B1 | 11/2018 | Metchik et al. |
| 10,136,993 | B1 | 11/2018 | Metchik et al. |
| 10,159,570 | B1 | 12/2018 | Metchik et al. |
| 10,231,837 | B1 | 3/2019 | Metchik et al. |
| 10,238,493 | B1 | 3/2019 | Metchik et al. |
| 10,245,144 | B1 | 4/2019 | Metchik et al. |
| D847,983 | S | 5/2019 | Ho et al. |
| 10,314,586 | B2 | 6/2019 | Greenberg et al. |
| 10,413,408 | B2 | 9/2019 | Krone et al. |
| 10,507,109 | B2 | 12/2019 | Metchik et al. |
| 10,517,726 | B2 | 12/2019 | Chau et al. |
| 10,524,792 | B2 | 1/2020 | Hernandez et al. |
| 10,595,997 | B2 | 3/2020 | Metchik et al. |
| 10,646,342 | B1 | 5/2020 | Marr et al. |
| 10,779,837 | B2 | 9/2020 | Lee et al. |
| D902,403 | S | 11/2020 | Marsot et al. |
| 10,856,988 | B2 | 12/2020 | McNiven et al. |
| 2002/0013571 | A1 | 1/2002 | Goldfarb et al. |
| 2002/0183787 | A1 | 12/2002 | Wahr et al. |
| 2003/0069593 | A1 | 4/2003 | Tremulis et al. |
| 2003/0167071 | A1 | 9/2003 | Martin et al. |
| 2004/0034365 | A1 | 2/2004 | Lentz et al. |
| 2004/0044350 | A1 | 3/2004 | Martin et al. |
| 2005/0267493 | A1 | 12/2005 | Schreck et al. |
| 2007/0038293 | A1 | 2/2007 | Goar St. et al. |
| 2017/0042546 | A1 | 2/2017 | Goldfarb et al. |
| 2017/0049455 | A1 | 2/2017 | Seguin |
| 2017/0239048 | A1 | 8/2017 | Goldfarb et al. |
| 2017/0265994 | A1 | 9/2017 | Krone |
| 2018/0021133 | A1 | 1/2018 | Barbarino |
| 2018/0036119 | A1 | 2/2018 | Wei et al. |
| 2018/0092661 | A1 | 4/2018 | Prabhu |
| 2018/0146964 | A1 | 5/2018 | Garcia et al. |
| 2018/0235657 | A1 | 8/2018 | Abunassar |
| 2018/0242976 | A1 | 8/2018 | Kizuka |
| 2018/0243086 | A1 | 8/2018 | Barbarino et al. |
| 2018/0325671 | A1 | 11/2018 | Abunassar et al. |
| 2018/0344460 | A1 | 12/2018 | Wei |
| 2018/0353181 | A1 | 12/2018 | Wei |

(56) References Cited

U.S. PATENT DOCUMENTS

| | | |
|---|---|---|
| 2018/0360457 A1 | 12/2018 | Ellis et al. |
| 2019/0053803 A1 | 2/2019 | Ketai et al. |
| 2019/0125536 A1 | 5/2019 | Prabhu et al. |
| 2019/0151041 A1 | 5/2019 | Ho et al. |
| 2019/0151089 A1 | 5/2019 | Wei |
| 2019/0159899 A1 | 5/2019 | Marsot et al. |
| 2019/0167197 A1 | 6/2019 | Abunassar et al. |
| 2019/0183571 A1 | 6/2019 | De Marchena |
| 2019/0209293 A1 | 7/2019 | Metchik et al. |
| 2019/0247187 A1 | 8/2019 | Kizuka |
| 2019/0274831 A1 | 9/2019 | Prabhu |
| 2019/0321597 A1 | 10/2019 | Van Hoven et al. |
| 2019/0343630 A1 | 11/2019 | Kizuka |
| 2019/0350702 A1 | 11/2019 | Hernandez |
| 2019/0350710 A1 | 11/2019 | Ketai et al. |
| 2019/0365536 A1 | 12/2019 | Prabhu |
| 2020/0000473 A1 | 1/2020 | Dell et al. |
| 2020/0060687 A1 | 2/2020 | Hernández et al. |
| 2020/0078173 A1 | 3/2020 | McNiven et al. |
| 2020/0113678 A1 | 4/2020 | McCann et al. |
| 2020/0121460 A1 | 4/2020 | Dale et al. |
| 2020/0121894 A1 | 4/2020 | Prabhu et al. |
| 2020/0187942 A1 | 6/2020 | Wei |
| 2020/0205829 A1 | 7/2020 | Wei |
| 2020/0245998 A1 | 8/2020 | Basude et al. |
| 2020/0261107 A1 | 8/2020 | Cohen |
| 2020/0281591 A1 | 9/2020 | Krone et al. |
| 2020/0323528 A1 | 10/2020 | Khairkhahan |
| 2020/0323549 A1 | 10/2020 | Goldfarb et al. |
| 2020/0323634 A1 | 10/2020 | Von Oepen et al. |
| 2020/0360018 A1 | 11/2020 | Dell et al. |
| 2020/0367871 A1 | 11/2020 | Van Hoven et al. |

FOREIGN PATENT DOCUMENTS

| | | |
|---|---|---|
| EP | 1 383 448 B1 | 6/2008 |
| FR | 2 768 324 A1 | 3/1999 |
| FR | 2 768 325 B1 | 11/1999 |
| WO | WO 91/01689 A1 | 2/1991 |
| WO | WO 92/12690 A1 | 8/1992 |
| WO | WO 94/018893 A1 | 9/1994 |
| WO | WO 96/32882 A1 | 10/1996 |
| WO | WO 97/27807 A1 | 8/1997 |
| WO | WO 98/07375 A1 | 2/1998 |
| WO | WO 99/07354 A2 | 2/1999 |
| WO | WO 99/13777 A1 | 3/1999 |
| WO | WO 99/15223 A1 | 4/1999 |
| WO | WO 00/03759 A2 | 1/2000 |
| WO | WO 00/60995 A2 | 10/2000 |
| WO | WO 01/28432 A1 | 4/2001 |
| WO | WO 03/020179 A1 | 3/2003 |
| WO | WO 03/049619 A2 | 6/2003 |
| WO | WO 2015/057289 A1 | 4/2015 |
| WO | WO 2016/178722 A1 | 11/2016 |
| WO | WO 2018/093663 A1 | 5/2018 |

WIDE CLIP WITH NONDEFORMABLE WINGS

CROSS-REFERENCE TO RELATED APPLICATIONS

This application claims the benefit of U.S. Provisional Patent Application No. 62/874,342 filed on Jul. 15, 2019, which is incorporated by reference herein in its entirety.

FIELD OF DISCLOSED SUBJECT MATTER

The disclosed subject matter is directed to medical devices for the endovascular, percutaneous or minimally invasive surgical treatment of bodily tissues, such as tissue approximation or valve repair. More particularly, the present disclosure relates to repair of valves of the heart and venous valves.

Surgical repair of bodily tissues can involve tissue approximation and fastening of such tissues in the approximated arrangement. When repairing valves, tissue approximation includes coapting the leaflets of the valves in a therapeutic arrangement which can then be maintained by fastening or fixing the leaflets. Such coaptation can be used to treat regurgitation, which commonly occurs in the mitral valve and in the tricuspid valve.

Mitral valve regurgitation is characterized by retrograde flow from the left ventricle of a heart through an incompetent mitral valve into the left atrium. During a normal cycle of heart contraction (systole), the mitral valve acts as a check valve to prevent flow of oxygenated blood back into the left atrium. In this way, the oxygenated blood is pumped into the aorta through the aortic valve. Regurgitation of the mitral valve can significantly decrease the pumping efficiency of the heart, placing the patient at risk of severe, progressive heart failure.

Mitral valve regurgitation can result from a number of different mechanical defects in the mitral valve or the left ventricular wall. The valve leaflets, the valve chordae connecting the leaflets to the papillary muscles, the papillary muscles or the left ventricular wall can be damaged or otherwise dysfunctional. Commonly, the valve annulus can be damaged, dilated, or weakened limiting the ability of the mitral valve to close adequately against the high pressures of the left ventricle.

DESCRIPTION OF RELATED ART

Treatments for mitral valve regurgitation can involve valve replacement or repair including leaflet and annulus remodeling, the latter generally referred to as valve annuloplasty. Another technique for mitral valve repair, which can be referred to as the "bow-tie" or "edge-to-edge" technique, can involve suturing adjacent segments of the opposed valve leaflets together is. Preferably, devices and systems for mitral valve repair can be utilized without open chest access and, rather, be capable of being performed either endovascularly, i.e., using devices, such as a catheter, advanced to the heart from a point in the patient's vasculature remote from the heart. Furthermore, such devices and systems should allow for repositioning and optional removal of a fixation device (e.g., a valve repair clip) prior to fixation to provide proper placement. Such devices and systems likewise can be useful for repair of tissues in the body other than heart valves.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter is directed to a fixation device for treating a patient.

In accordance with the disclosed subject matter, a fixation device for fixation of leaflets of a heart valve includes a central assembly and at least one arm moveably coupled to the central assembly. The at least one arm includes a body portion having a first end and a second end and a longitudinal axis defined therebetween, the second end being moveable between a closed position and an open position, the body portion having opposing body lateral sides, each body lateral side extending between the first end and the second end, the body portion having a body portion width defined between the opposing body lateral sides. The at least one arm further includes first and second nondeformable wing extensions, each wing extension extending laterally from a respective lateral side, each wing extension having a lateral outer edge, wherein a maximum arm width is defined between the outer lateral edge of the first wing extension and the outer lateral edge of the second wing extension. The fixation device further includes at least one gripping element moveable relative to the at least one arm to capture a native leaflet therebetween.

The maximum arm width can be between about 1.40 and 1.60 times the body portion width. The maximum arm width can be about 1.50 times the body portion width. The first and second wing extensions each can have a first end edge and a second end edge, wherein the first end edge extends between the respective body lateral side and the outer lateral edge and is located proximate the first end of the body portion, and the second end edge extends between the respective body lateral side and the outer lateral edge and is located proximate the second end of the body portion. The first end edge extends from the body lateral side at a first end angle defined between the first end edge and the longitudinal axis, wherein the first end angle can be between 30 and 60 degrees. The first end angle can be 45 degrees. The second end edge extends from the respective body lateral side at a second end angle defined between the second end edge and the longitudinal axis, wherein the second end angle can be between 30 and 60 degrees. The second end angle can be 45 degrees. A first end lead dimension is defined along the body portion by a distance between the first end of the body portion and an intersection of the first end edge and the respective body lateral side, wherein the first end lead dimension can be between about 0.15 inch and 0.25 inch. The first end lead dimension can be 0.19 inch.

A second end lead dimension is defined along the body portion by a distance between the second end of the body portion and an intersection of the second end edge and the respective body lateral side, wherein the second end lead dimension can be between about 0.05 inch and 0.15 inch. The second end lead dimension can be 0.09 inch. A first end lead dimension is defined along the body portion by a distance between the first end of the body portion and an intersection of the first end edge and the respective body lateral side, and a second end lead dimension is defined along the body portion by a distance between the second end of the body portion and an intersection of the second end edge and the respective body lateral side, and the second end lead dimension can be less than one third of the first end lead dimension. The first end edge has a first end fillet at an intersection with the respective body lateral side, wherein the first end fillet has a radius of curvature between one and eleven times a thickness of the arm. The arm can have a thickness of about 0.015 inch. The first end fillet can have a radius of curvature between about 0.02 inch and 0.165 inch. The first end fillet can have a radius of curvature of 0.12 inch. The first end fillet can have a radius of curvature eight times the thickness of the arm. The second end edge has a second end fillet at an intersection with the body lateral side, wherein the second end fillet can have a radius of curvature between one and eleven times a thickness of the arm.

The arms can each have a thickness of about 0.015 inch. The second end fillet can have a radius of curvature between about 0.015 inch and 0.165 inch. The second end fillet can have a radius of curvature of 0.012 inch. The second end fillet can have a radius of curvature eight times the thickness of the arm. The first end edge can have a first end round at an intersection with the outer lateral edge, wherein the first end round can have a radius of curvature between one and eleven times a thickness of the arm. The arms can each have a thickness of about 0.015 inch. The first end round can have a radius of curvature between about 0.02 inch and 0.165 inch. The first end round can have a radius of curvature of 0.12 inch. The first end round can have a radius of curvature eight times the thickness of the arm. The second end edge has a second end round at an intersection with the outer lateral edge, wherein the second end round can have a radius of curvature between one and eleven times a thickness of the arm. The arms can each have a thickness of about 0.015 inch. The second end round can have a radius of curvature between about 0.02 inch and 0.165 inch.

The second end round can have a radius of curvature of 0.12 inch. The second end round has a radius of curvature eight times the thickness of the arm. A second end edge extends from the second end of the body portion at a second end angle defined between the second end edge and the longitudinal axis, wherein the second end angle can be between 30 and 60 degrees. The wing first end edge, lateral outer edge, and second end edge can form a continuous complex curve. The at least one arm can further have a recessed trough along the longitudinal axis, and the trough can have a trough width sized greater than a width of the at least one gripping element. The trough width can increase from the first end of the body portion to the second end of the body portion. The first and second wing extensions and the body portion can be a single piece. Each first and second wing extension in end cross-section can extend laterally from the respective body lateral side and then can extend perpendicularly to the outer lateral edge. The fixation device can comprise a second arm moveably coupled to the central assembly, the second arm comprising a body portion having a first end and a second end, the second end being moveable between a closed position and an open position, wherein in the closed position, the at least one arm can be sized to surround the second arm on at least three sides of the at least one arm. Each first and second wing extension in end cross-section can extend at a wing extension angle defined between the wing extension and a reference axis extending through the opposing body lateral sides of each respective first and second wing extension, wherein the wing extension angle can be between 125 and 145 degrees. The wing extension angle can be about 135 degrees.

The at least one gripping element can have at least one friction element along a length thereof. The at least one gripping element can have a plurality of friction elements along the length thereof, wherein when the at least one gripping element is located proximate the at least one arm the plurality of friction elements are disposed along a length defined between the intersection of the first end edge and the respective body lateral side, and the intersection of the second end edge and the respective body lateral side. The fixation device can further include a second arm moveably coupled to the central assembly, the second arm comprising a second body portion having a first end and a second end, the second end being moveable between a closed position and an open position. The fixation device can further include a second gripping element moveable relative to the second arm to capture a native leaflet therebetween.

In accordance with the disclosed subject matter, a kit of fixation devices for fixation of leaflets of a heart valve includes a plurality of fixation devices. Each fixation device includes a central assembly and at least one arm moveably coupled to the central assembly. The at least one arm, includes a body portion having a first end and a second end, the second end being moveable between a closed position and an open position, and a longitudinal axis defined therebetween, the body portion having opposing body lateral sides, each body lateral side extending between the first end and the second end, the body portion having a body portion width defined between the opposing body lateral sides. The fixation device further includes at least one gripping element moveable relative to the at least one arm to capture a native leaflet therebetween. The at least one arm has differing length and width dimensions between the plurality of fixation devices.

DETAILED DESCRIPTION

Figure 1:
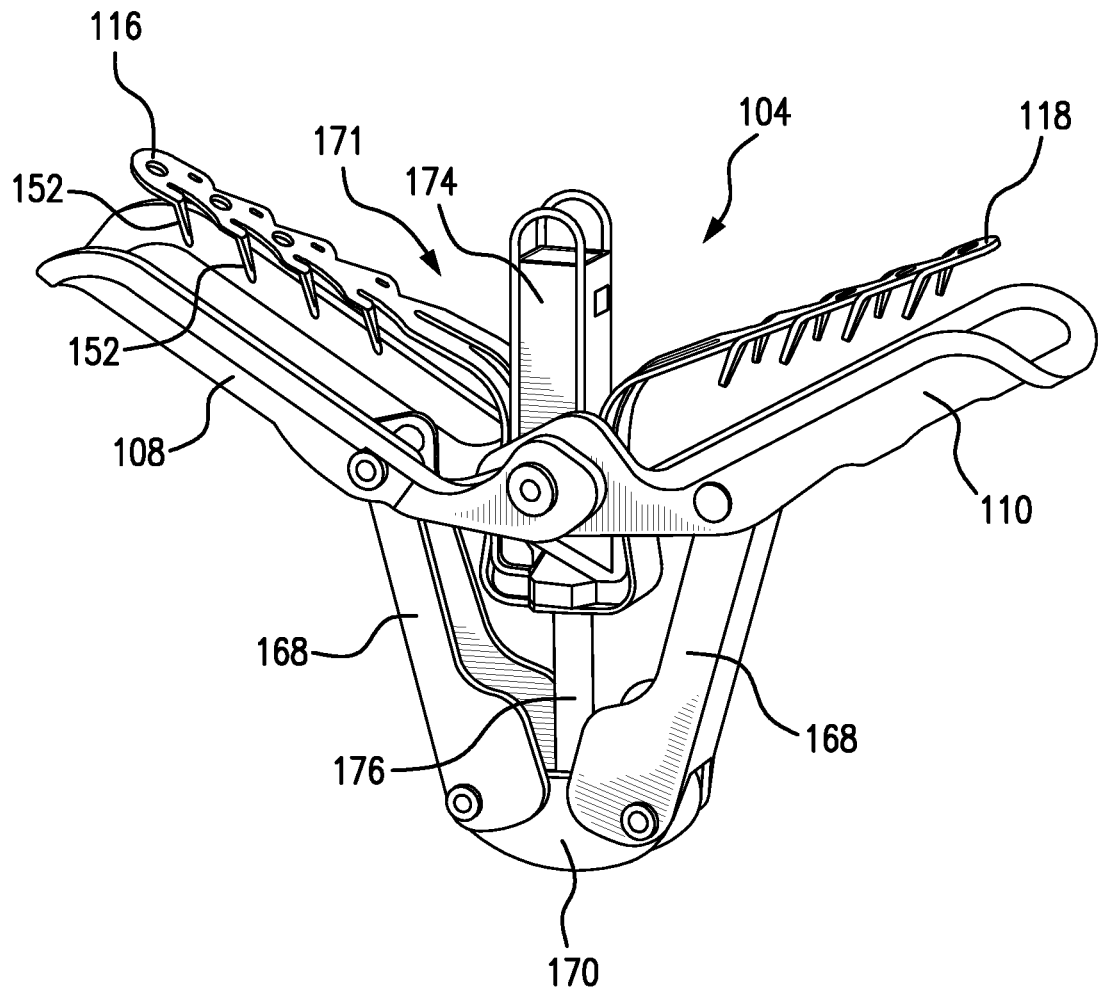
FIG. 1 is a perspective view of an exemplary embodiment of a fixation device for use in accordance with the disclosed subject matter.

Reference will now be made in detail to the various exemplary embodiments of the disclosed subject matter, exemplary embodiments of which are illustrated in the accompanying drawings.

The fixation device for use with the disclosed subject matter provides an edge-to-edge transcatheter valve repair option for patients having various conditions, including regurgitant mitral valves or tricuspid valves. Transcatheter (trans-septal) edge-to-edge valve repair has been established using a fixation device, such as the MitraClip Transcatheter Mitral Valve Repair device. These fixation devices generally are configured to capture and secure opposing native leaflets using two types of leaflet contacting elements. The first element is a sub-valvular arm (also known as a distal element or fixation element) to contact the ventricular side of a native leaflet to be grasped. With the arm positioned underneath to stabilize the native leaflet in a beating heart, a second gripping element (e.g., a proximal element) can be lowered or moved into contact with the atrial side of the native leaflet to capture the leaflet therebetween. Once each opposing leaflet is captured by a respective arm and gripper element, the fixation device can be closed by moving the arms toward a center of the fixation device such that the leaflets are brought into coaptation, which results in a reduction in valvular regurgitation during ventricular systole. Furthermore, a covering can be provided on the arms and/or gripper elements to facilitate tissue ingrowth with the captured leaflets.

Additional details of exemplary fixation devices in accordance with the disclosed subject matter are set forth below. Furthermore, various patents and published applications disclose additional details of such fixation devices and related operations, for example, U.S. Pat. No. 7,226,467 to Lucatero et al., U.S. Pat. No. 7,563,267 to Goldfarb et al., U.S. Pat. No. 7,655,015 to Goldfarb et al., U.S. Pat. No. 7,736,388 to Goldfarb et al., U.S. Pat. No. 7,811,296 to Goldfarb et al., U.S. Pat. No. 8,057,493 to Goldfarb et al., U.S. Pat. No. 8,303,608 to Goldfarb et al., U.S. Pat. No. 8,500,761 to Goldfarb et al., U.S. Pat. No. 8,734,505 to Goldfarb et al., U.S. Pat. No. 8,740,920 to Goldfarb et al., U.S. Pat. No. 9,510,829 to Goldfarb et al., U.S. Pat. No. 7,635,329 to Goldfarb et al., U.S. Patent Application Publication No. 2017/0042546 to Goldfarb et al., U.S. Patent Application Publication No. 2017/0239048 to Goldfarb et al., U.S. Patent Application Publication No. 2018/0325671; the entirety of the contents of each of these patents and published applications is incorporated herein by reference.

In grasping tissue and leaflet capture for mitral valve disease, certain patient conditions and anatomies, such as those associated with larger dynamic gaps between leaflet tips, can create challenges for capture. As such, there is an opportunity for a fixation device capable of bridging larger gaps, such as in functional mitral regurgitation (FMR), while also providing more reliable leaflet capture, for example in cases of dynamic, chaotic, or overly severe degenerative mitral regurgitation (DMR), such as in cases of Barlow's Syndrome. Particularly, the size and configuration of the arm of the fixation device can significantly improve performance. However, such modifications can be configured to account for numerous factors to produce desired clinical benefit and still be deliverable transvascularly. For example, a typical guide catheter size for delivery can have an inner diameter of about 0.22 inch or less.

Furthermore, when positioned within a patient, the guide catheter defines a tortious path through which the fixation device can be delivered. As such, the fixation device can be configured to have an overall profile capable of such delivery through the corresponding bends and turns of the guide catheter.

Additionally, and as previously noted, the fixation device is configured to capture or grasp a leaflet between the arm and the gripping element. When in the closed position, it can be beneficial to provide further capture of adjacent leaflets positioned between two arms in the final implanted condition. Such capture can be a function of the contact patch area of the leaflets as defined by the width and configuration of the arms. Furthermore, it can be beneficial to provide each arm with sufficient rigidity to reduce or prevent deformation along the lateral edges, which can further facilitate grasping and retainment of the leaflets, e.g., by providing secure contact with the leaflet between the closed arms. In this manner, the nondeformable arms can create areas of suitable compression along the respective lateral edges to retain the leaflets therebetween and assist the native tissue ingrowth in the corresponding covering.

Generally, and as set forth in greater detail below, the disclosed subject matter provided herein includes a fixation device for fixation of leaflets of a heart valve including a central assembly and at least one arm moveably coupled to the central assembly. The at least one arm includes a body portion having a first end and a second end and a longitudinal axis defined therebetween, the second end being moveable between a closed position and an open position, the body portion having opposing body lateral sides, each body lateral side extending between the first end and the second end, the body portion having a body portion width defined between the opposing body lateral sides. The at least one arm further includes first and second nondeformable wing extensions, each wing extension extending laterally from a respective lateral side, each wing extension having a lateral outer edge, wherein a maximum arm width is defined between the outer lateral edge of the first wing extension and the outer lateral edge of the second wing extension. The fixation device further includes at least one gripping element moveable relative to the at least one arm to capture a native leaflet therebetween.

Figure 2:
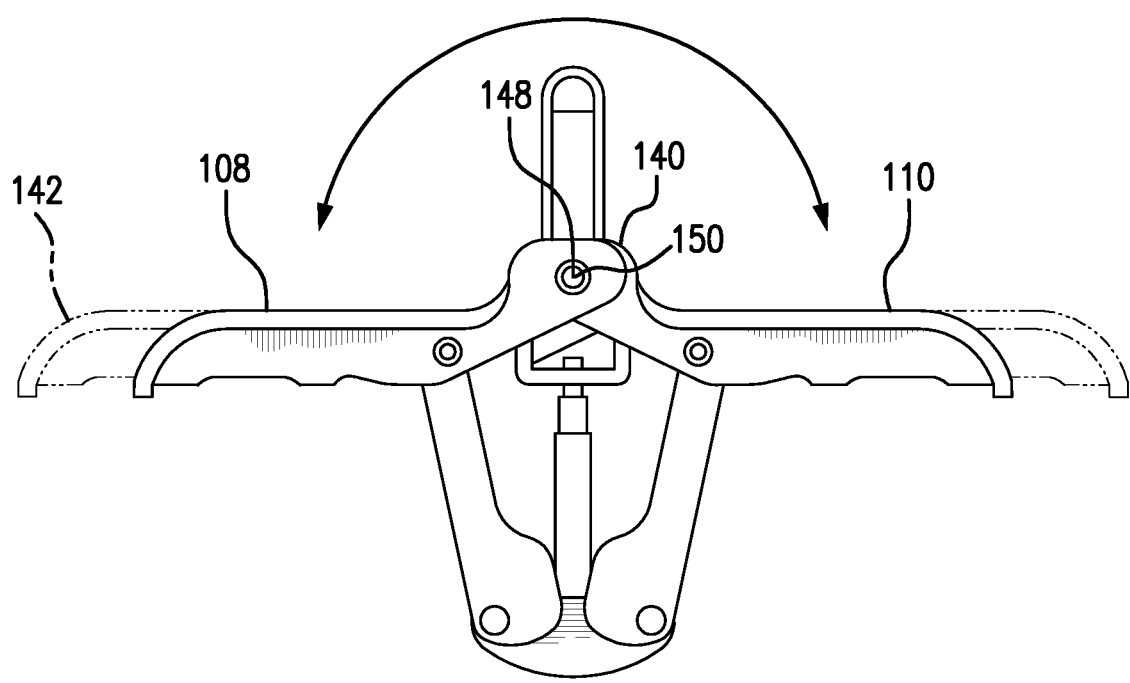
FIG. 2 is a front view of the fixation device of FIG. 1 at a different position, wherein optional arms of greater length are depicted with dashed lines.

Referring to FIGS. 1-2 for the purpose of illustration and not limitation, a fixation device 104 for fixation of native leaflets of a heart valve is disclosed herein. The fixation device as embodied herein includes a central assembly 171. The central assembly 171 can include various central components for operation and release of the fixation device for example, a coupling member 174 as described further in the disclosures of the patents and applications incorporated by reference herein. The fixation device as depicted further includes at least one arm 108 moveably coupled to the central assembly 171. As shown, the fixation device can further include a second arm 110 moveably coupled to the central assembly 171. For purpose of understanding and reference only, FIGS. 1, 2, 3A-3C and 4A-4B depict the arms without the wing extensions of the disclosed subject matter.

With reference to FIG. 2, and further in accordance with the disclosed subject matter, each arm 108, 110 can be rotatable about a respective axis point 148, 150 between closed, open and inverted positions, as well as any position therebetween. Furthermore, the arms 108, 110 can be selected from a range of suitable lengths, wherein the appropriate length can be selected by the physician or health care provider, for example after inspection of a patient. For purpose of comparison, a first length of each arm 108, 110 is depicted in FIG. 2 in solid lines, and a second longer length of each arm of the disclosed subject matter is depicted in dashed lines. The arms in solid lines can be an entirely separate arm with a different length as compared to the arm in dashed lines.

Figure 3A:
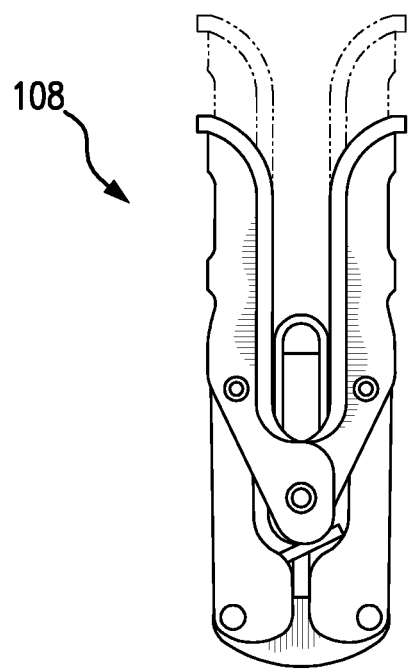
FIGS. 3A-3C are front views of the fixation device of FIG. 1 at various positions, wherein optional arms of greater length are depicted with dashed lines.
Figure 3B:
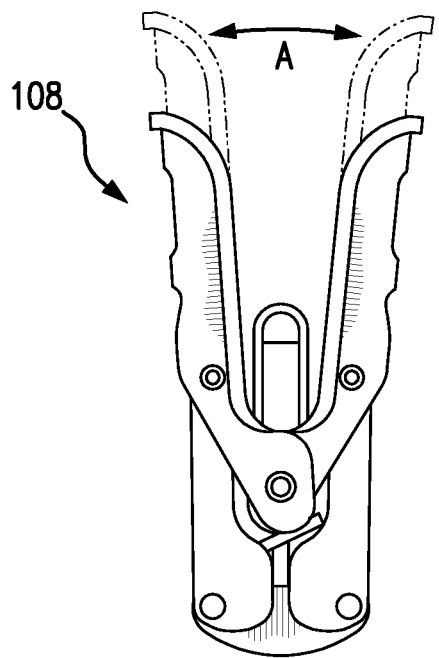
Figure 3C:
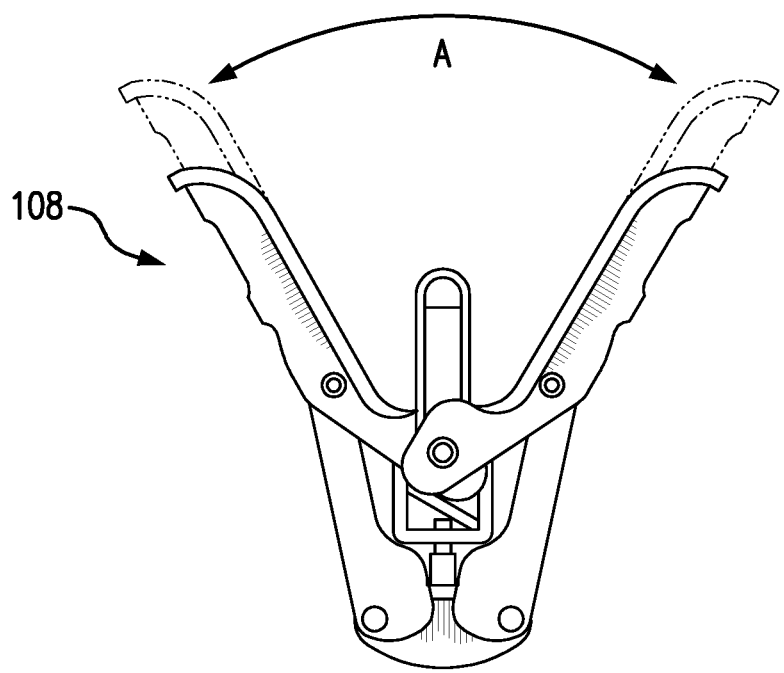

As depicted herein in FIGS. 3A-3C, various positions of the fixation device 104 are depicted for purpose of illustration and not limitation. Elongated arms of the disclosed subject matter are illustrated in dashed lines for comparison to shorter arms. In FIG. 3A, the fixation device is in the closed position, wherein the arms are positioned axially in alignment, e.g., vertically or nearly vertically as shown. FIGS. 3B and 3C illustrate the arms positioned with an angle A between each other. In FIG. 3B, A is about 10 degrees and in FIG. 3C A is about 60 degrees. As disclosed herein, the fixation device is in the closed position when A is about 30 or less degrees. Although not depicted, the arms can continue to open until A exceeds 180 degrees, e.g., inverted.

Figure 4A:
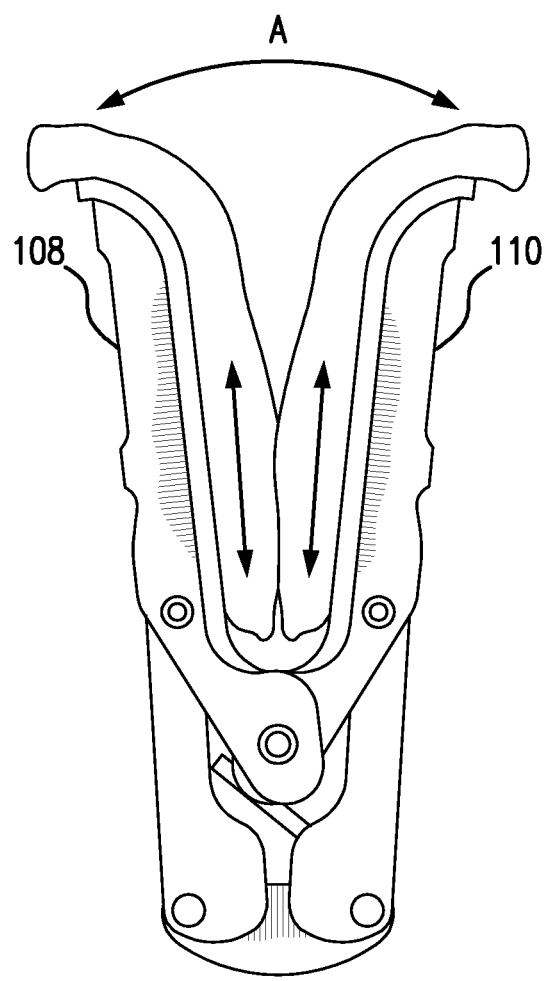
FIG. 4A is a front schematic view of the fixation device of FIG. 1 having leaflets captured therein.
Figure 4B:
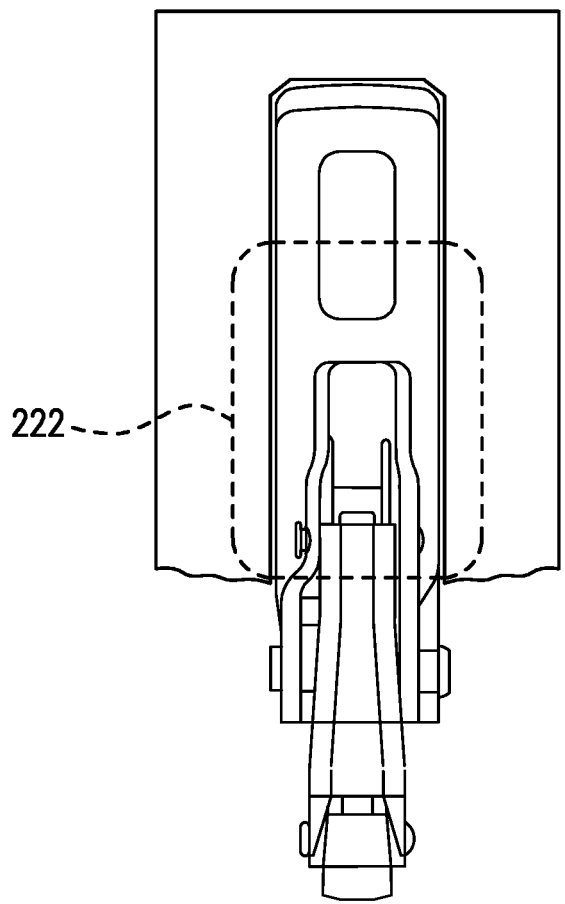
FIG. 4B is a side view of the fixation device of FIG. 1 schematically depicting a contact patch area.

As previously noted generally, and as set forth in further detail below, a native leaflet can be captured between each arm and a respective gripping element. Each arm can then be moved toward its closed position. In this manner, adjacent leaflets can further be captured between the arms in the closed position. For example, and for illustration only, FIGS. 4A-4B show the fixation device 104 depicted with the arms 108, 110 at an angle A of about 10 to 30 degrees with two leaflets captured therebetween, wherein each leaflet is captured between an arm and a respective gripping element (gripping element not shown). As illustrated in FIG. 4B, a contact patch area 222 depicted in dashed lines and is defined by the area of tissue captured between the arms. The contact patch area 222 can depict a tissue-to-tissue contact patch area defined by area of a leaflet in contact with a counterpart leaflet. As previously noted, FIG. 4B depicts the contact patch area 222 when each arm does not include wing extensions and the fixation device is oriented an angle A of about 10 to 30 degrees.

In accordance with the disclosed subject matter an arm configuration is provided to increase contact patch area and capture of adjacent leaflets between two arms of the fixation device in a closed or final implanted position. Additionally, the arm can be configured with the contact patch area spaced from the first end of the arm, such as intermediate along the length of the arm or proximate the second end of the arm. Furthermore, the arm can be nondeformable, particularly along lateral edges to facilitate secondary capture of the leaflets between the arms. For example, the arms can be formed of cobalt chromium alloy (Elgiloy or L605) or other metallic materials, such as stainless steel, titanium, nickel titanium (Nitinol). Further, the arms can be formed from or include any class of polymers such as semi-crystalline polylactic acid, polyurethane, or PLGA, or other polymeric or composite materials processed to behave in a rigid or semi-rigid manner.

Figure 5:
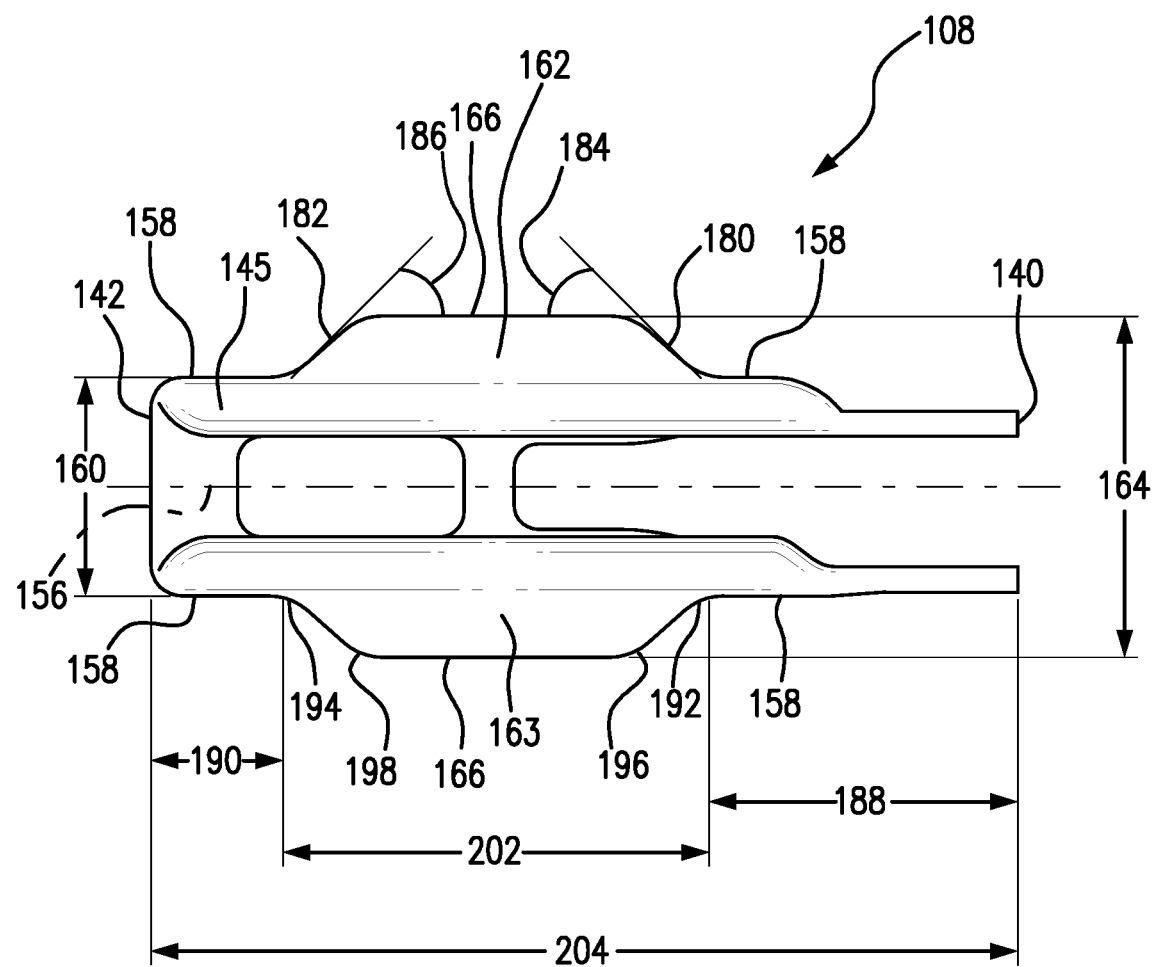
FIG. 5 is a plan view of an exemplary embodiment of an arm for the fixation device of FIG. 1 in accordance with the disclosed subject matter.

For purpose of illustration and not limitation, a plan view of an arm for a fixation device in accordance with the disclosed subject matter is depicted in FIG. 5. Although FIG. 5 and other figures throughout this application depict a single arm for clarity, it is understood that each feature of the at least one arm 108 can apply similarly to one or more additional arm, such as, an opposing second arm 110. As shown in FIG. 5, the arm includes a body portion 145 having a first end 140 and a second end 142 and a longitudinal axis 156 defined therebetween, the second end being moveable between a closed position and an open position. The body portion 145 has opposing body lateral sides 158, each body lateral side 158 extending between the first end 140 and the second end 142, and the body portion 145 has a body portion width 160 defined between the opposing body lateral sides 158.

In accordance with the disclosed subject matter, arm 108 (and any additional arms) can further include first and second nondeformable wing extensions 162, 163, each wing extension extending laterally from a respective lateral side 158. As embodied herein, each wing extension 162, 163 has a lateral outer edge 166. Each wing extension 162, 163 can include or be formed from a biocompatible, nondeformable material, such as Elgiloy. Particularly, and as embodied herein, the first and second wing extensions 162, 163 and the body portion 145 are a single piece. The wing extensions 162, 163 can generally be flat-shaped solid structures having no holes or openings therein. As embodied herein, a maximum arm width 164 is defined between the outer lateral edge 166 of the first wing extension 162 and the outer lateral edge 166 of the second wing extension 163. The maximum arm width 164 can be between about 1.40 and 1.60 times the body portion width. For example, the maximum arm width 164 can be about 1.50 times the body portion width. For purpose of illustration, the maximum arm 164 width can be between about 0.196 inch to 0.236 inch, and preferably about 0.203 inch, and the body portion width can be between about 0.118 inch to 0.157 inch, and preferably about 0.135 inch.

As further depicted in FIG. 5, and as embodied herein, the first and second wing extensions 162, 163 can each have a first end edge 180 and a second end edge 182, and as embodied herein, the first end edge 180 can extend between the respective body lateral side 158 and the outer lateral edge 166. As depicted, the first end edge 180 can be located closer to or proximate the first end 140 of the body portion. The second end edge 182 can extend between the respective body lateral side 158 and the outer lateral edge 166. The second end edge can be located closer to or proximate the second end 142 of the body portion. Thus, the first end edge 180 can be located closer than the second end edge 182 to the first end 140 of the body portion. Likewise, the second end edge 182 can be located closer than the first end edge 180 to the second end 142 of the body portion. The first end edge 180 can extend from the body lateral side 158 at a first end angle 184 defined between the first end edge 180 and the longitudinal axis 156, and as embodied herein, the first end angle 184 is between 15 and 60 degrees. For example, the first end angle 184 can be 45 degrees. By providing the first end angle with a smaller angle, drag forces generated as the fixation device passes through a guide catheter can be reduced or eliminated whereas a larger angle can increase the tissue capture effectiveness of the wing extensions. As such, the first end angle can be selected based upon the desired preference.

For each wing extension 162, 163, the second end edge 182 can extend from the respective body lateral side 158 at a second end angle 186 defined between the second end edge 182 and the longitudinal axis 156, wherein the second end angle 186 is between 15 and 60 degrees. For example, the second end angle 186 can be 45 degrees. The second end angle can be selected to reduce or minimize drag forces, for example if the fixation device is configured to be retracted into and back through a curved guide catheter. The reduced drag forces provided by such an angle can reduce or avoid damage to a fabric or porous covering placed on the clip arm.

With continued reference to FIG. 5, a first end lead dimension 188 is defined along the body portion 145 by a distance between the first end 140 of the body portion and an intersection of the first end edge 180 and the respective body lateral side 158. As embodied herein, the first end lead dimension 188 can be between about 0.15 inch and 0.25 inch, such as 0.19 inch. Likewise, a second end lead dimension 190 can be defined along the body portion 145 by a distance between the second end 142 of the body portion and an intersection of the second end edge 182 and the respective body lateral side 158. As embodied herein, the second end lead dimension 190 can be between about 0.05 inch and 0.15 inch, such as 0.09 inch. In accordance with another aspect of the disclosed subject matter, the second end lead dimension 190 can be less than one third of the first end lead dimension 188. In this manner, the corresponding contact patch area can be disposed at a distance from the first end, and if desired, closer to the second end of the arm.

With further reference to FIG. 5, a wing extension length dimension 202 can be defined by the distance between the first end lead dimension 188 and the second end lead dimension 190. An arm length dimension 204 can be defined by the distance between the first end 140 of the body portion and the second end 142 of the body portion. Adjustment of these dimensions can modify the corresponding contact patch area and length of the lateral edge in engagement with tissue for capture of leaflets between two closed arms.

Figure 6A:
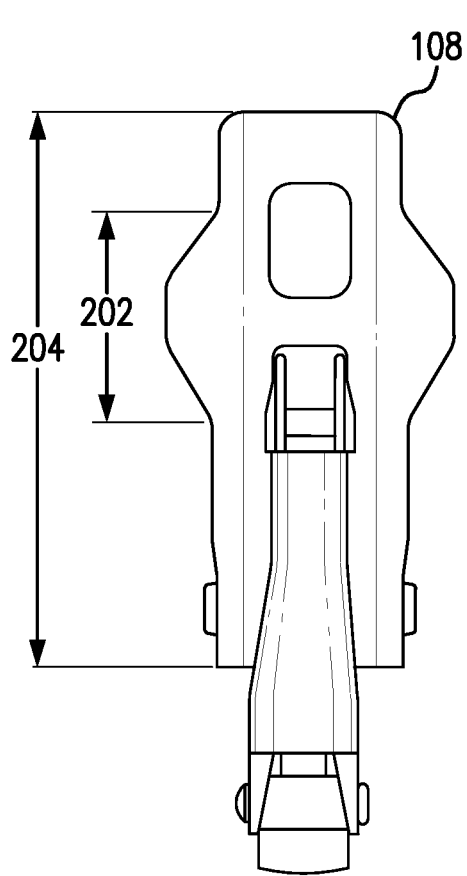
FIGS. 6A-6B are comparative side views of alternative embodiments of arms for the fixation device of FIG. 1, in accordance with the disclosed subject matter.
Figure 6B:
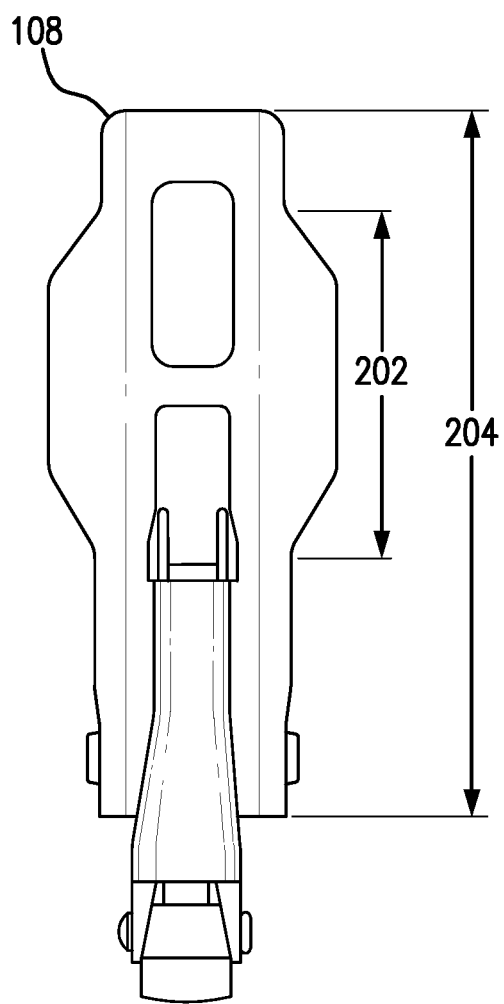

For example, and for purpose of illustration, FIGS. 6A-6B depict for comparison the arms 108, 110 with varied parameters (e.g., length). The arms can be provided with the desired parameters as selected by a user, for example after inspection of a patient. For purpose of illustration and not limitation, an arm as shown in FIG. 6A can have an arm length 204 of about 0.422 inch and a wing extension length 202 between about 0.074 inch and about 0.174 inch. As embodied herein, and with a thickness of about 0.015 inch, the wing extensions can add an increased mass of only about 9.3% to each arm as compared to a similar arm with no wing extensions, while increasing overall surface area by about 18%. With reference to FIG. 6B, an arm can have an arm length 204 of about 0.522 inch and a wing extension length 202 between about 0.173 inch and about 0.273 inch. As embodied herein, and with a thickness of about 0.015 inch, the wing extensions can add an increased mass of only about 12.6% to each arm as compared to a similar arm with no wing extensions, while increasing overall surface area by about 28%. As embodied herein, and for purpose of illustration and not limitation, the wing extension length 202 can change with the length of the arm 204, whereas the first lead in 188 and the second lead in 190 dimensions can remain constant.

For purpose of illustration and comparison of the actual coaptation dimensions of arms with and without wing extensions, a test was performed wherein arms in a fixation device were closed around artificial leaflets at an angle A of about 10 degrees and pressure film was inserted therein. The pressure film provided an estimate of the actual coaptation length, width, and area for arms of different lengths. Arms having a length 204 of about 0.422 inch and no wing extension as embodied herein had a coaptation length of about 0.278 inch, width of about 0.176 inch, and area of about 0.0487 inch$^2$. Arms having a length 204 of about 0.522 inch and no wing extension as embodied herein had a coaptation length of about 0.386 inch, width of about 0.182 inch, and area of about 0.0704 inch$^2$. Arms having a length 204 of about 0.422 inch and a wing extension as embodied herein has a coaptation length of about 0.278 inch, width of about 0.262 inch, and area of about 0.0730 inch$^2$. Arms having a length 204 of about 0.522 inch and a wing extension as embodied herein has a coaptation length of about 0.387 inch, width of about 0.269 inch, and area of about 0.104 inch$^2$. While the numbers produced in this test are beneficial at least for purpose of comparison, the implanted device can include a covering, such as a porous polyester covering, which can affect the actual coaptation dimensions of an implanted device.

Referring back to FIG. 5, the first end edge 180 can have a first end fillet 192 at an intersection with the respective body lateral side 158. As embodied herein, the first end fillet 192 has a radius of curvature between one and eleven times a thickness of the arm 108. For example, the arm 108 can have a thickness of about 0.015 inch, and the first end fillet 192 can have a radius of curvature between about 0.015 inch and 0.165 inch, such as 0.12 inch. As embodied herein, for example for improved manufacturability of arms having an arm length 204 under about 0.522 inch, for example an arm length of about 0.422 inch, the first end fillet 192 can have a radius of curvature of about 0.09 inch. In an alternative embodiment, the first end fillet 192 can have a radius of curvature of about 0.030 inch.

The second end edge 182 can have a second end fillet 194 at an intersection with the body lateral side 158, and as embodied herein, the second end fillet 194 can have a radius of curvature between one and eleven times a thickness of the arm 108. For example, the arm 108 can have a thickness of about 0.015 inch and the second end fillet 194 can have a radius of curvature between about 0.015 inch and 0.165 inch, such as 0.12 inch. As embodied herein, for example for improved manufacturability of arms having an arm length 204 under about 0.522 inch, for example an arm length of about 0.422 inch, the second end fillet 194 can have a radius of curvature of about 0.09 inch. In an alternative embodiment, the second end fillet 194 can have a radius of curvature of about 0.030 inch.

Additionally, and as further depicted for illustration and not limitation, the first end edge 180 can have a first end round 196 at an intersection with the outer lateral edge 166. As embodied herein, the first end round 196 has a radius of curvature between one and eleven times a thickness of the arm 108. For example, the arm 108 can have a thickness of about 0.012 inch to about 0.018 inch, such as about 0.015 inch, and the first end round 196 can have a radius of curvature between about 0.015 inch and 0.165 inch, such as 0.12 inch. The first end round 196 can have a radius of curvature eight times the thickness of the arm 108. As embodied herein, by altering the first end round to include a large radius of curvature, drag forces can be reduced or eliminated as the fixation device passes through a guide catheter lumen, where a smaller radius of curvature can increase the tissue capture effectiveness of the wing extensions. The reduced drag forces provided by rounded corners (increased radius curvature) can maintain or improve the integrity of a fabric or porous covering placed on the clip arm. As embodied herein, for example for improved manufacturability of arms having an arm length 204 under about 0.522 inch, for example an arm length of about 0.422 inch, the first end round 196 can have a radius of curvature of about 0.09 inch. In an alternative embodiment, the first end round 196 can have a radius of curvature of about 0.030 inch.

The second end edge 182 can have a second end round 198 at an intersection with the outer lateral edge 166. As embodied herein, the second end round 198 can have a radius of curvature between one and eleven times a thickness of the arm 108. For example, the arm 108 can have a thickness of about 0.012 inch to about 0.018 inch, such as about 0.015 inch, and the second end round 198 can have a radius of curvature between about 0.02 inch and 0.165 inch, such as 0.12 inch. The second end round 198 can have a radius of curvature eight times the thickness of the arm 108. As embodied herein, by altering the second end round 198, drag forces can be reduced or eliminated, for example to configure the fixation device to be retracted into and back though a curved guide catheter. As embodied herein, for example for improved manufacturability, arms having an arm length 204 under about 0.522 inch, for example an arm length of about 0.422 inch, the second end round 198 can have a radius of curvature of about 0.09 inch. In an alternative embodiment, the second end round 198 can have a radius of curvature of about 0.030 inch.

Figure 7A:
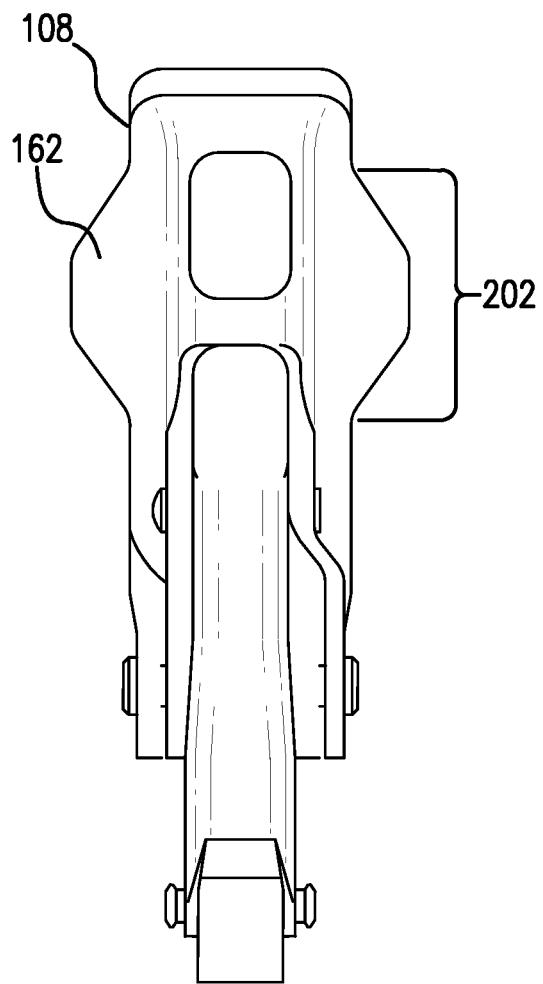
FIG. 7A is a side view of a portion of the fixation device of FIG. 1, with an alternative embodiment of an arm in accordance with the disclosed subject matter.
Figure 7B:
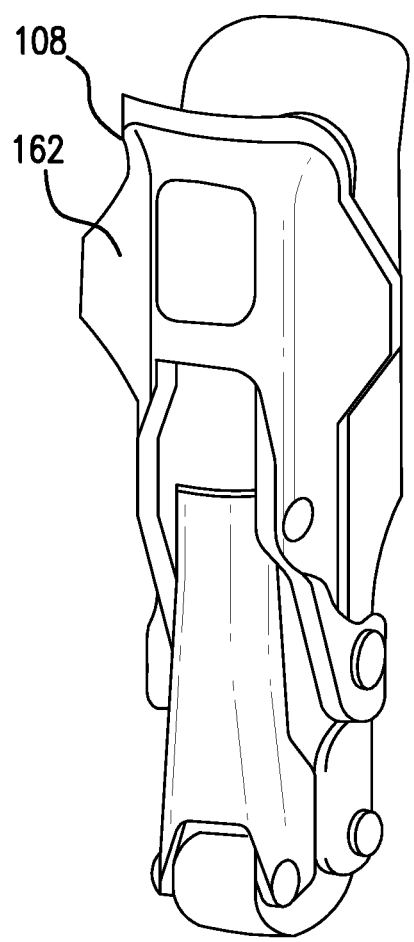
FIG. 7B is a perspective view including the alternative embodiment of the arm of FIG. 7A.
Figure 8A:
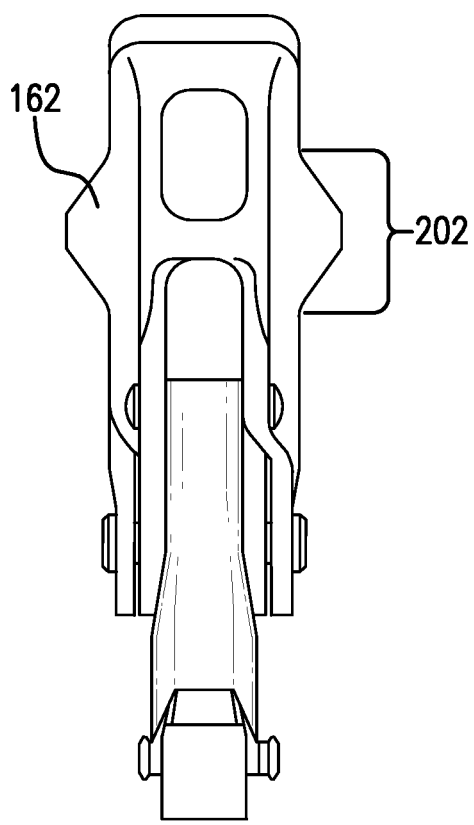
FIG. 8A is a side view of a portion of the fixation device of FIG. 1, with another exemplary embodiment of an arm in accordance with the disclosed subject matter.
Figure 8B:
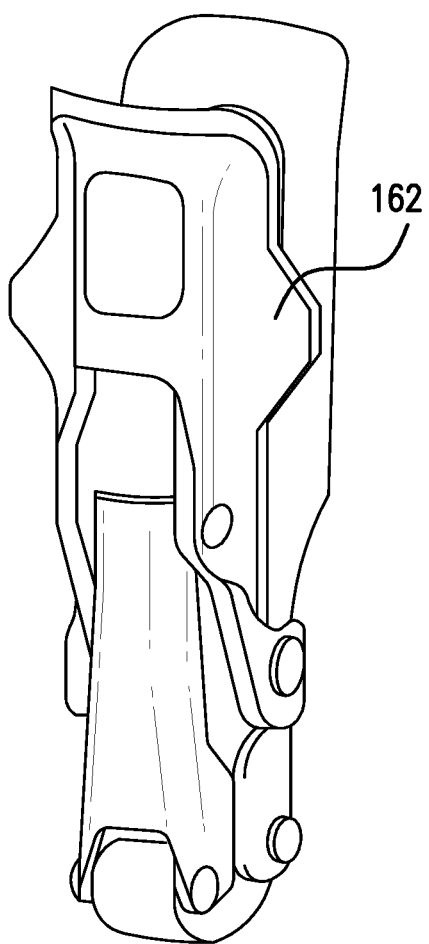
FIG. 8B is a perspective view including the exemplary embodiment of the arm of FIG. 8A.
Figure 9A:
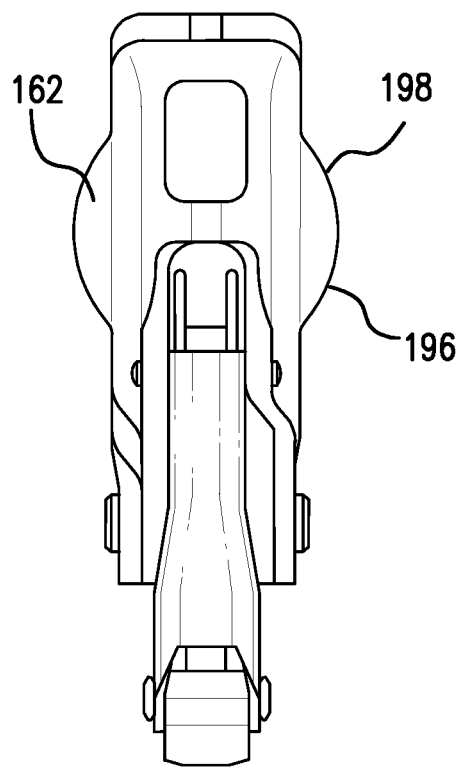
FIG. 9A is a side view of a portion of the fixation device of FIG. 1, with another exemplary embodiment of an arm in accordance with the disclosed subject matter.
Figure 9B:
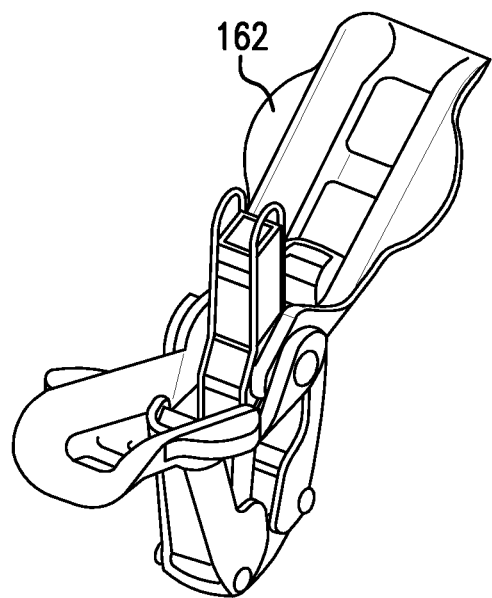
FIG. 9B is a perspective view including the exemplary embodiment of the arm of FIG. 9A in an open position.

The features of the arm can be varied or selected as desired to accommodate performance criteria. For example, and not limitation, various alternative arms 108 are disclosed in FIGS. 7A-10B. That is, the dimensions of the wing extensions 162 can be selected to provide the desired performance of each arm (e.g., to capture and retain a leaflet, to track through and retract into a guide catheter, etc.). For example, as compared to the dimensions of the wing extension 162 disclosed in FIG. 5, the wing extension 162 disclosed in FIGS. 7A-7B has a reduced wing extension length 202 dimension, and the wing extension 162 disclosed in FIGS. 8A-8B has an even further reduced wing extension length 202 dimension while maintaining other dimensions (e.g., radius of curvature of fillets and rounds). Referring to FIGS. 9A-9B, the disclosed wing extensions 162 have increased first and second end round 196, 198 dimensions, as compared to the wing extension 162 dimensions previously disclosed. The wing first end edge 180, lateral outer edge 166, and second end edge 182 can form a continuous complex curve. The embodiment of FIG. 10A-10B has similar end rounds and fillets as FIGS. 9A-9B, but an extended wing extension length 202.

Figures 10A, 10B:
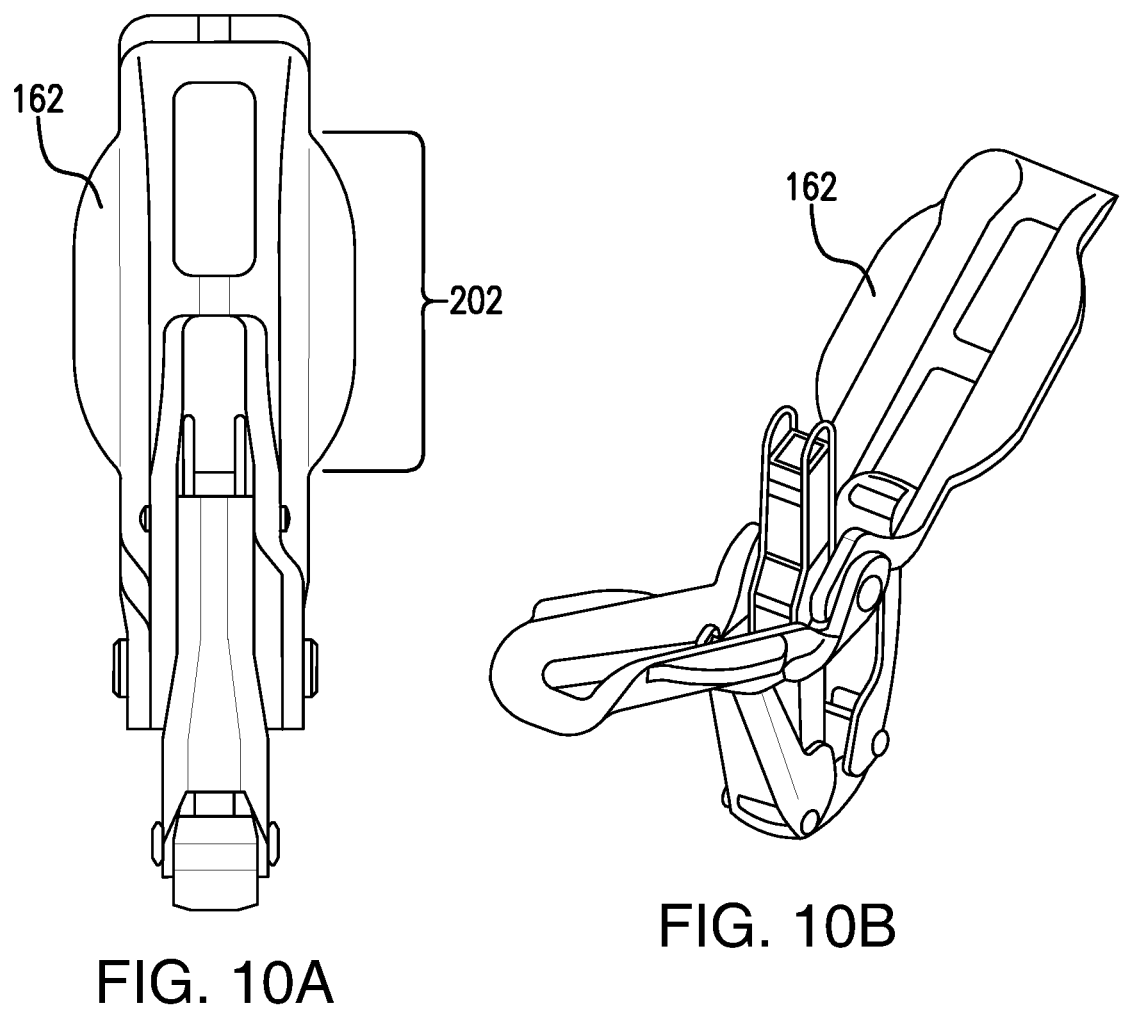
FIG. 10A is a side view of a portion of the fixation device of FIG. 1, with another exemplary embodiment of an arm in accordance with the disclosed subject matter.
FIG. 10B is a perspective view including the exemplary embodiment of the arm of FIG. 10A in an open position.
Figure 11A:
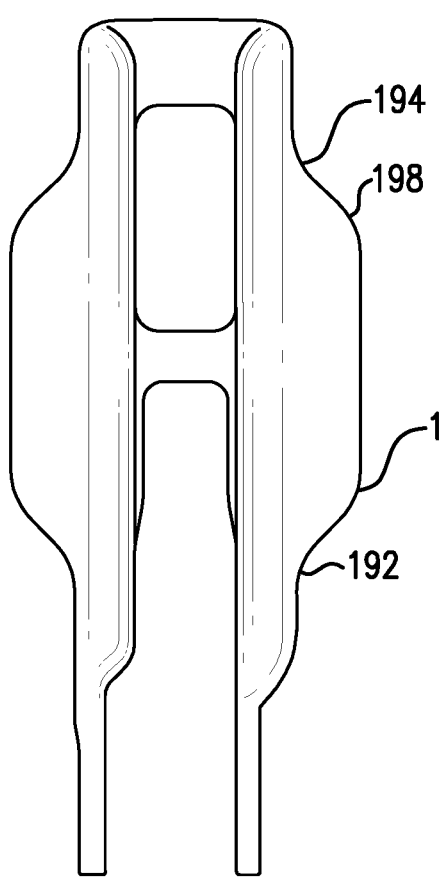
FIGS. 11A-11B are comparative plan views of different embodiments of arms for the fixation device of FIG. 1 in accordance with the disclosed subject matter.
Figure 11B:
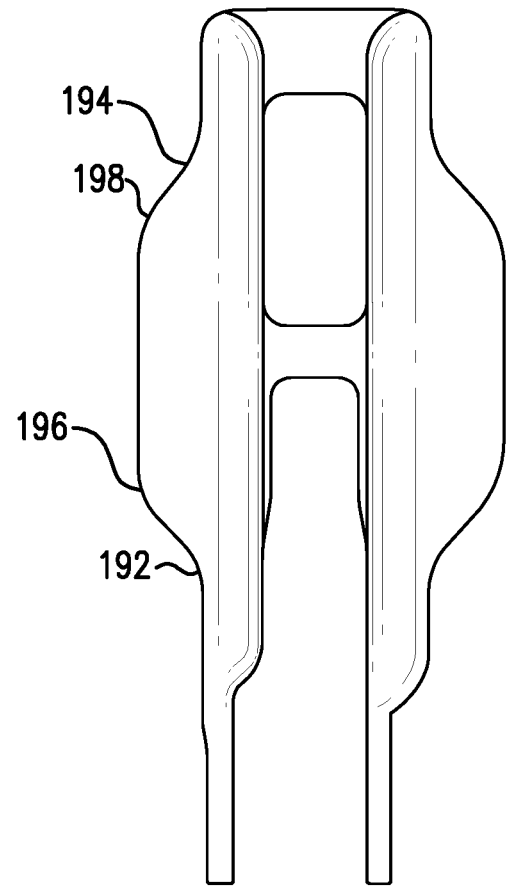

For purpose of comparison, FIGS. 11A-11B depict exemplary arms similar to the arm of FIG. 5 and FIG. 10A to demonstrate suitable fillets and rounds of various dimensions. In FIGS. 11A-11B, each arm has a length of about 0.047 inch, a width of about 0.203 inch, and a thickness of about 0.015 inch. In FIG. 11A, the first end fillet 192 radius of curvature is about 0.120 inch (i.e., eight times the thickness), the first end round 196 radius of curvature is about 0.120 inch (i.e., eight times the thickness), the second end fillet 194 radius of curvature is about 0.120 inch (i.e., eight times the thickness), and the second end round 198 radius of curvature is about 0.120 inch (i.e., eight times the thickness). In FIG. 11B, the first end fillet 192 radius of curvature is about 0.030 inch (i.e., two times the thickness), the first end round 196 radius of curvature is about 0.120 inch (i.e., eight times the thickness), the second end fillet 194 radius of curvature is about 0.030 inch (i.e., two times the thickness), and the second end round 198 radius of curvature is about 0.120 inch (i.e., eight times the thickness). Larger end round and fillet dimensions can reduce or eliminate abrupt edges or corners, which can reduce stress concentrations and reduce or minimize undesired interactions with the covering during delivery and deployment of the fixation device.

Figure 12:
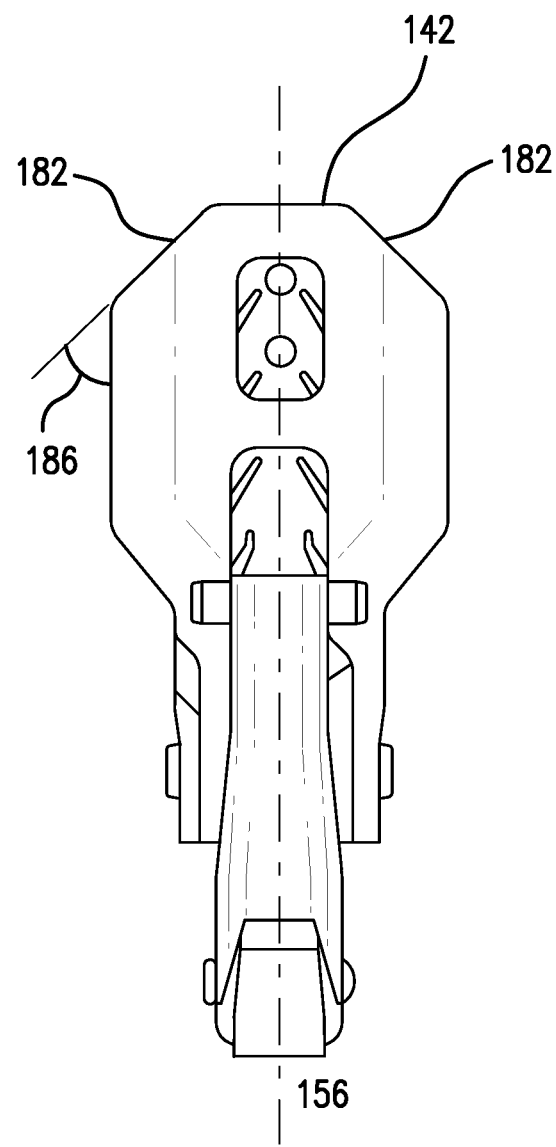
FIG. 12 is a side view of a portion of the fixation device of FIG. 1, with another exemplary embodiment of an arm in accordance with the disclosed subject matter.

As further embodied herein in FIG. 12, an alternative arm configuration, referenced as a duck bill arm configuration, is disclosed for purpose of illustration and not limitation. In the duck bill arm configuration, the second end edge 182 of each wing extension extends from the second end 142 of the body 145 at a second end angle 186 defined between the second end edge 182 and the longitudinal axis 156, and as embodied herein, the second end angle 186 is between 15 and 60 degrees. The second end angle forms a taper that reduces undesirable focal stresses sharp contact points that can occur under various circumstances with squared clip arms.

Referring back to FIG. 1, and as discussed herein, the fixation device 104 further includes at least one gripping element 116 moveable relative to the at least one arm 108 to capture a second native leaflet therebetween. In accordance with the disclosed subject matter, each arm can be configured to define or have a trough aligned along the longitudinal axis. The trough has a width sized greater than a width of the gripper element so as to receive the gripper element therein.

The fixation device can further include a second gripping element 118 moveable relative to the second arm 110 to capture a native leaflet therebetween. Further, in accordance with the disclosed subject matter, the at least one gripping element 116 can have at least one friction element 152 along a length thereof. As embodied herein, each gripping element includes a plurality of friction elements 152, which can be disposed in rows. For example, each gripping element 116, 118 can have at least four rows of friction elements 152. The friction elements 152 can allow for improved tissue engagement during leaflet capture. This gripping element design can increase the assurance that single device leaflet attachment will not occur during a procedure. To adjust the fixation device after an initial leaflet capture, the arms can be opened, the gripping element can be raised vertically, and tissue can disengage from the fixation device, facilitating re-grasp and capture.

With continued reference to FIG. 1, and as further embodied herein, each gripping element 116, 118 can be biased toward each respective arm 108, 110. Prior to leaflet capture, each gripping element 116, 118 can be moved inwardly toward a longitudinal center of the device (e.g., away from each respective arm 108, 110) and held with the aid of one or more gripper element lines (not shown), which can be in the form of sutures, wires, nitinol wire, rods, cables, polymeric lines, or other suitable structures. The sutures can be operatively connected with the gripping elements 116, 118 in a variety of ways, such as by being threaded through loops disposed on the gripping elements 116, 118.

Figure 13A:
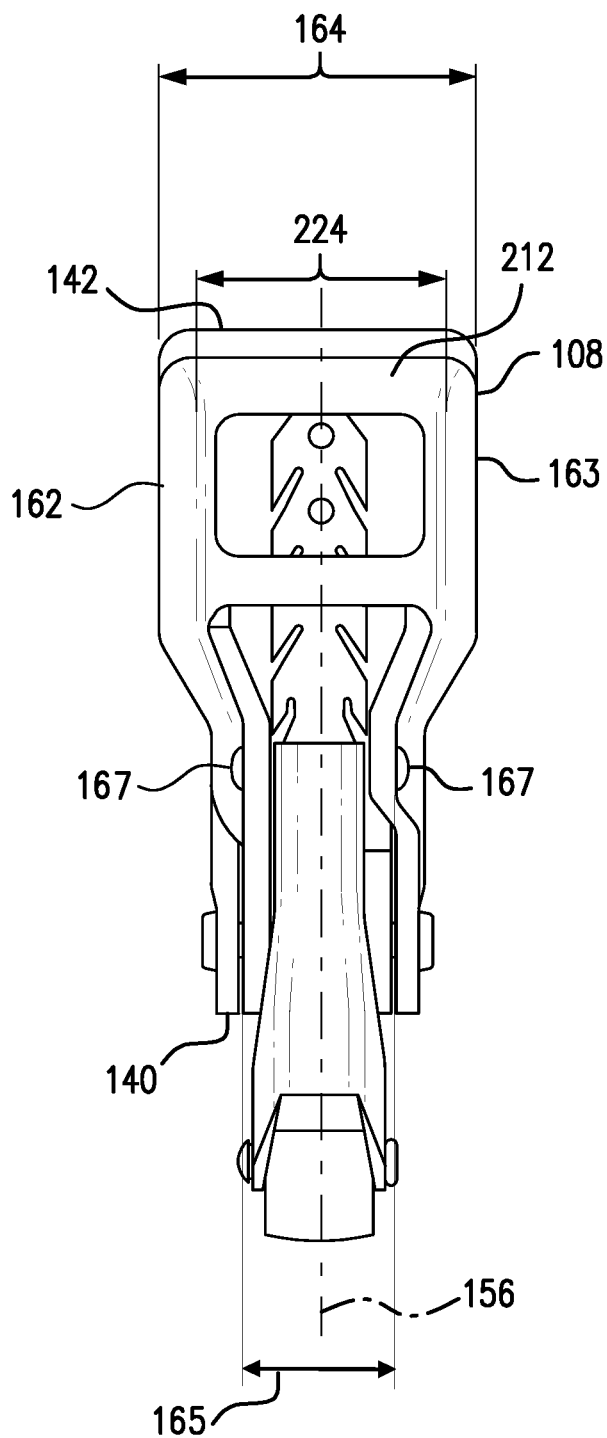
FIG. 13A is a side view of a portion of the fixation device of the FIG. 1, with an alternative embodiment of an arm in accordance with the disclosed subject matter.
Figure 13B:
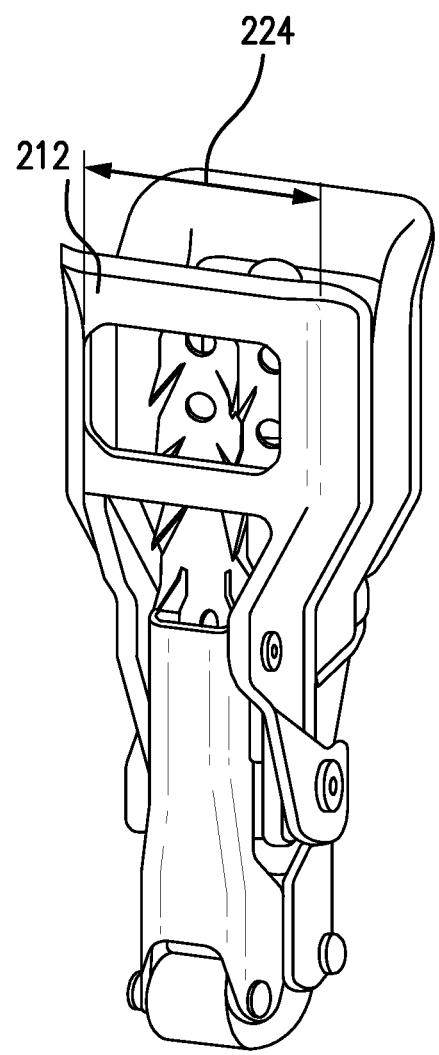
FIG. 13B is a perspective view including the alternative embodiment of the arm of FIG. 13A.
Figure 15:
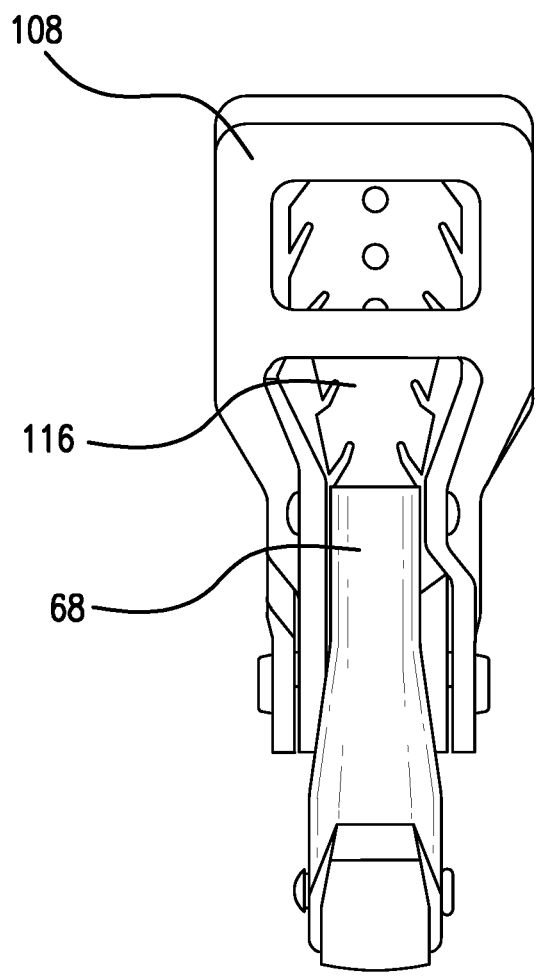
FIG. 15 is a side view of a portion of the fixation device of FIG. 1, with another exemplary embodiment of an arm and gripper in accordance with the disclosed subject matter.

In accordance with another aspect of the disclosed subject matter, and with reference to FIGS. 13A-13B, the at least one arm 108 can have a recessed trough 212 along the longitudinal axis 156, and as embodied herein, the trough 212 has a trough width sized to receive the at least one gripping element 116. Particularly and with reference to FIG. 13A, the trough width can increase from the first end 140 of the body portion to the second end 142 of the body portion so as to have a maximum trough width 224 corresponding with location along the arm of the maximum arm width 164. In this manner, the widened trough 212, e.g., proximate the second end, can accommodate a widened gripping element, as illustrated in FIG. 15. A wider arm 108 and gripping element 116 can generally increase the capturability and retainment of the fixation device 104 to leaflets. Furthermore, if desired, although not shown, the second end edge of the wing extension can be angled similar to the duck bill embodiment of FIG. 12.

With continued reference to FIG. 13A, a connection width 165 of the arm is defined between outer lateral edges of the arm 108 at a location proximate a pin connection 167. The pin connection 167 can pivotally connect the leg 168 to the arm 108. The pin connection 167 can comprise riveting, welding, swaging, or other joining methods. In one embodiment, the maximum arm width 164 can be between about 1.5 times and 2.5 times the connection width 165. For example, the maximum arm width 164 can be about 2 times the connection width 165.

Figure 14:
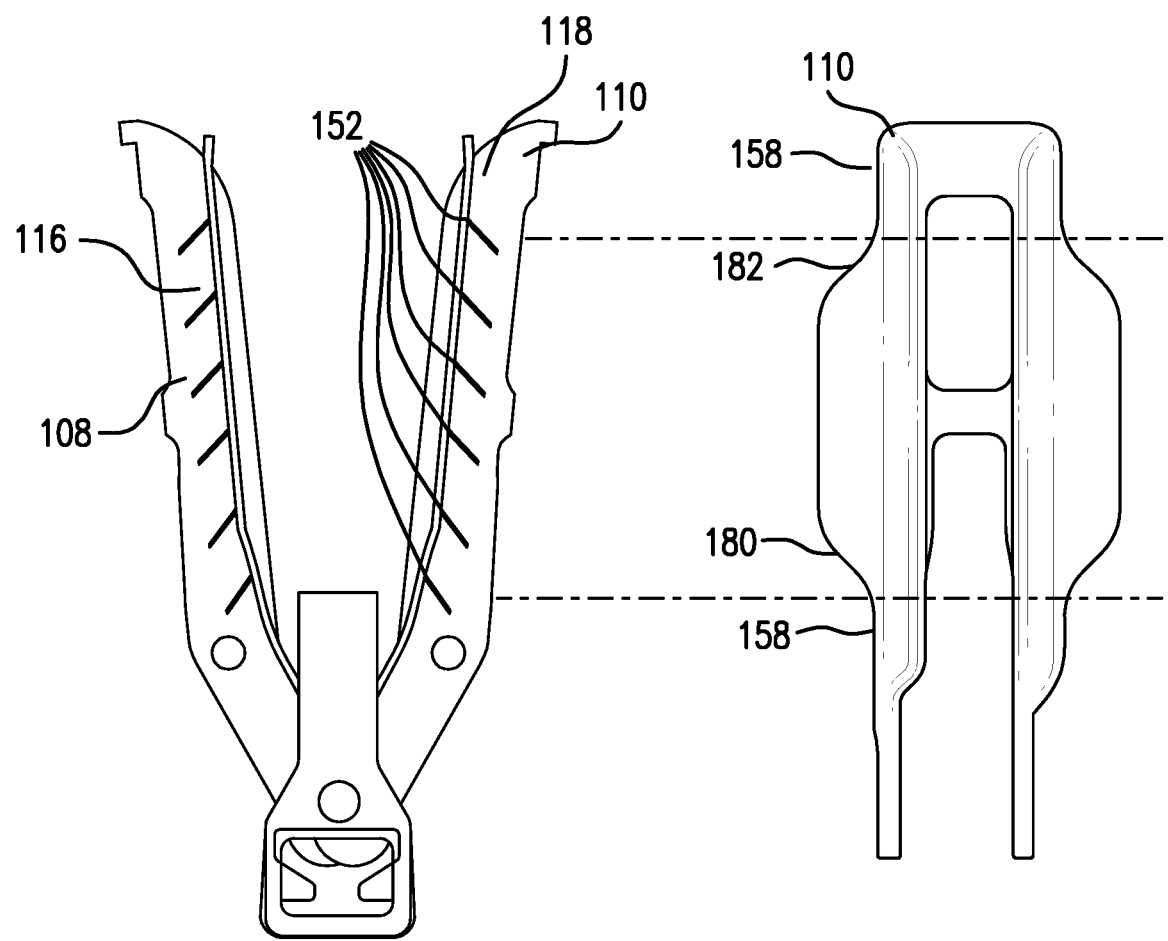
FIG. 14 is a schematic view of a portion of the fixation device of FIG. 1 taken in front cross-section aligned with a plan view of a corresponding arm of the disclosed subject matter.

Additionally, as discussed herein, and as shown in FIG. 14, the at least one gripping element 116 can have at least one friction element 152 along a length thereof. The at least one gripping element 116 can have a plurality of friction elements 152 along the length thereof. In accordance with another aspect of the disclosed subject matter, the arm and respective gripper element can be aligned such that when the at least one gripping element 116 is received within the trough 212 of the at least one arm 108, the plurality of friction elements 152 are disposed along a length defined between the intersection of the first end edge 180 and the respective body lateral side 158, and the intersection of the second end edge 182 and the respective body lateral side 158 of the respective wing extensions. This configuration can further increase the leaflet tissue securement at the region of the wing features. In the configuration embodied herein, frictional elements disposed at the top and bottom of each wing can reduce or eliminate tissue erosion by providing more secure engagement at the desired locations.

Figure 16A:
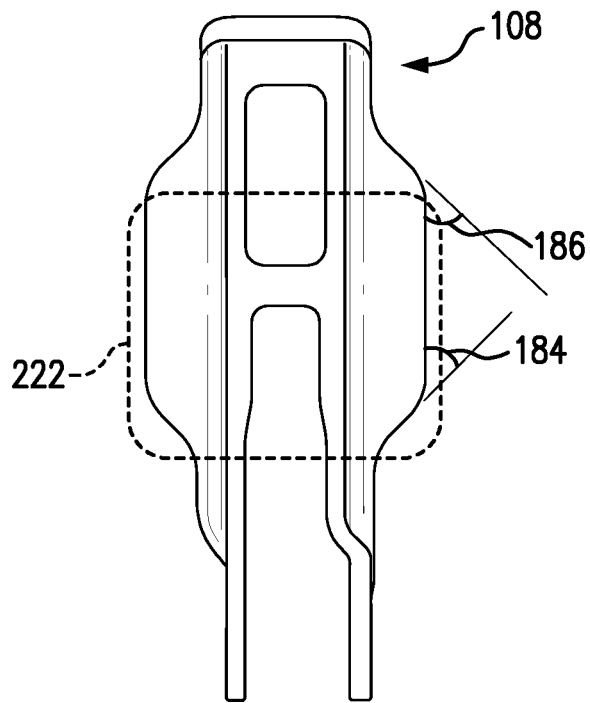
FIGS. 16A-16C are plan views of alternative embodiments of arms schematically depicting corresponding contact patch areas in accordance with the disclosed subject matter.
Figure 16B:
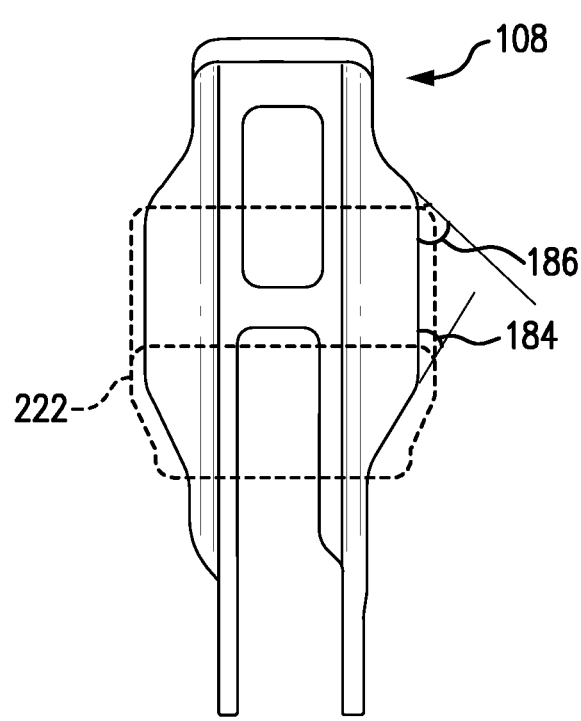
Figure 16C:
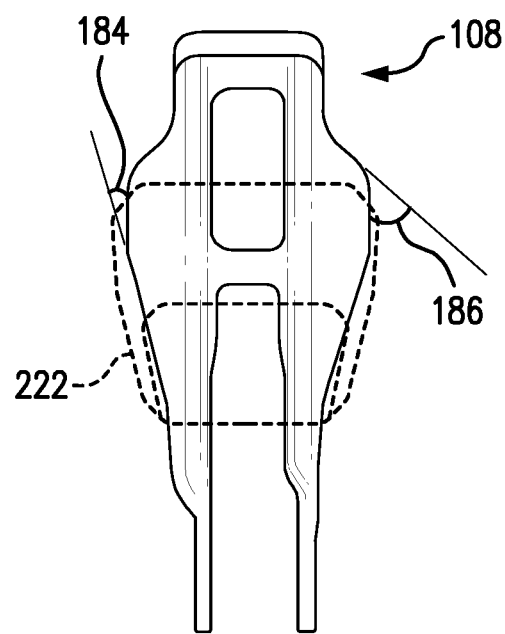

As further embodied herein, various alternative arms 108 having corresponding contact patch areas 222 are depicted in dashed lines in FIGS. 16A-16C. FIG. 16A depicts an arm 108 wherein each wing extension has a first end angle 184 of about 45 degrees and a second end angle 186 also of about 45 degrees. When a fixation device having the arms depicted in FIG. 16A is oriented at an angle A of about 10 degrees, the resulting contact patch area 222 is approximately square with about 150% of the area relative to a contact patch area for a fixation device without wing extensions.

In accordance with the disclosed subject matter, the contact patch area 222 can be modified by a user by adjusting the orientation of A. In each of FIGS. 16B-16C, two different contact patch areas are depicted in dashed lines. As shown, a relatively small contact patch area is illustrated within the boundary of a larger contact patch area. For purpose of illustration and understanding, and not limitation, the larger contact patch area corresponds to a fixation device oriented at an angle A of about 10 degrees, and the smaller contact patch area corresponds to a fixation device oriented at an angle A of about 30 degrees. FIGS. 16B-16C depict arms 108 having a second end angle 186 that is more tapered than the second end angle in FIG. 16A. FIG. 16B depicts an arm 108 wherein each wing extension has a first end angle 184 of about 35 degrees and a second end angle 186 of about 45 degrees. When a fixation device having the arms depicted in FIG. 16B is oriented at an angle A of about 10 degrees, the resulting contact patch area 222 is depicted by the larger contact patch area, which has about 133% of the area relative to a contact patch area for a fixation device without wing extensions. FIG. 16C depicts an arm 108 wherein each wing extension has a first end angle 184 of about 15 degrees and a second end angle 186 of about 45 degrees. When a fixation device having the arms depicted in FIG. 16B is oriented at an angle A of about 10 degrees, the resulting contact patch area 222 is depicted by the larger contact patch area, which has about 125% of the area relative to a contact patch area for a fixation device without wing extensions.

As shown, each of the smaller contact patch areas 222 illustrated in FIGS. 16B-16C, which correspond to a fixation device oriented at an angle A of about 30 degrees, show a contact patch area that is reduced as compared to each larger contact patch area, which correspond to a fixation device oriented at an angle A of about 10 degrees. As embodied herein, in FIG. 16C, both the width and the length of the smaller contact patch area 222 is reduced. As such, a fixation device having arms with reduced first end angles 184 can allow a user to reduce the contact patch area with a relatively small change in the angle A between the arms. As embodied herein, when the first end angles 184 are reduced, the width of the contact patch area 222, in addition to the length, changes as a function of the angle A of the arms 108, 110. Such a change in arm structure can allow a user to make a relatively slight change in arm angle and produce a relatively large change in the contact patch area, which can impact the trans-valvular gradient and thus reduce or avoid the risk of mitral stenosis. As such, a tapered arm can be beneficial for accommodating mitral regurgitation, for example in circumstances wherein a patient valve is relatively small (e.g., mitral valve area less than 0.620 inch squared) and the regurgitant jet is relatively wide (e.g., 0.295 inch or greater). In this manner, a tapered arm can provide selectable dimensions by location of fixation to allow for tunable properties of the device.

Figure 19:
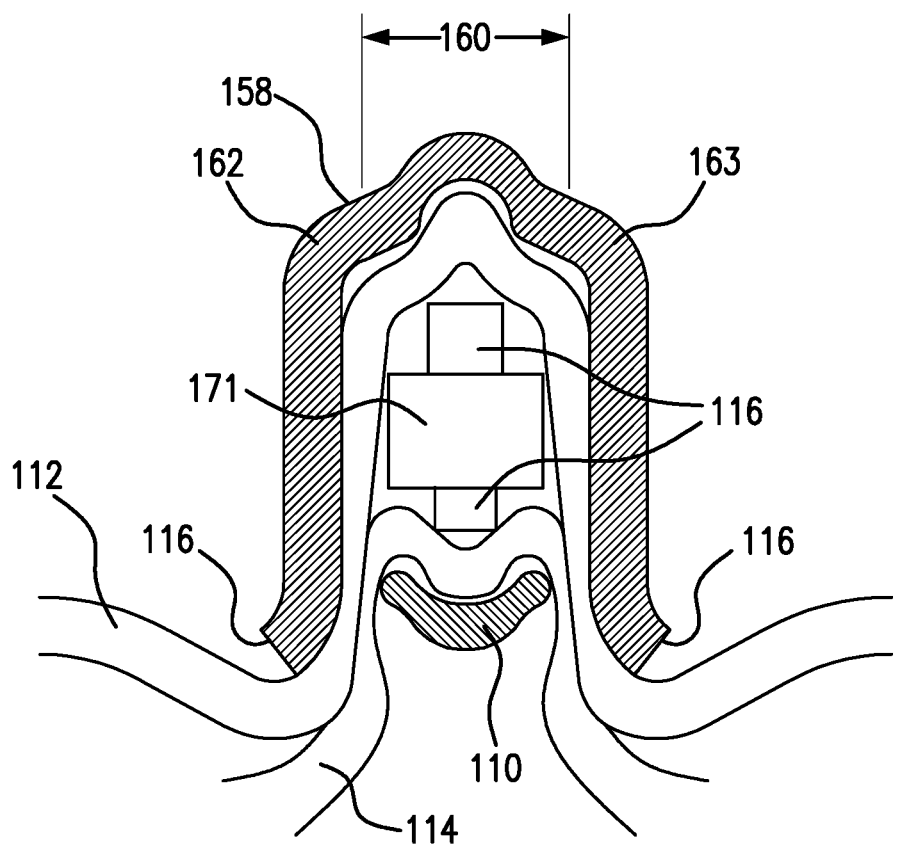
FIG. 19 is a schematic illustrating an end cross-section view of an additional alternative embodiment of an arm in accordance with the disclosed subject matter.
Figure 20A:
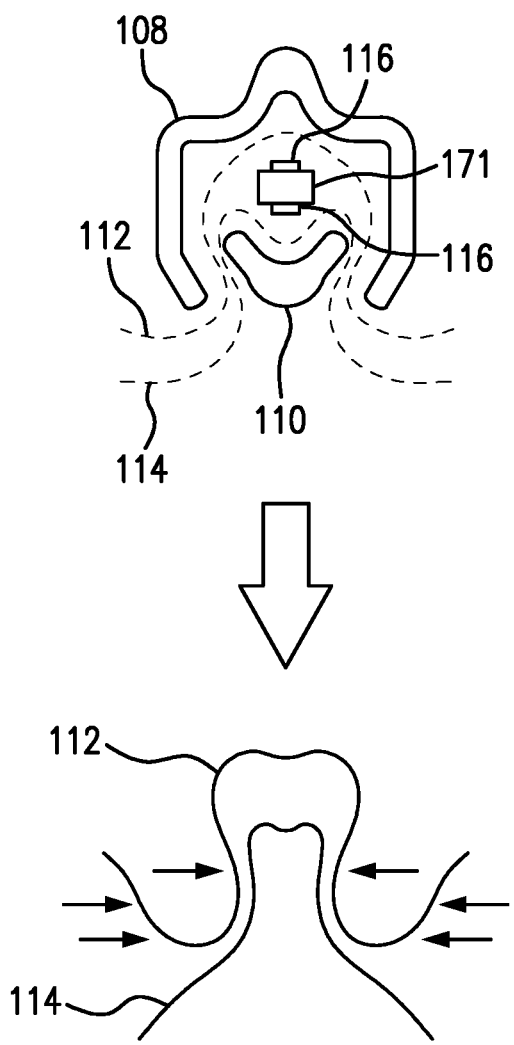
FIGS. 20A-20B are schematics illustrating end cross-section views of alternative embodiments of arms and corresponding leaflet coaptation pattern in accordance with the disclosed subject matter.
Figure 20B:
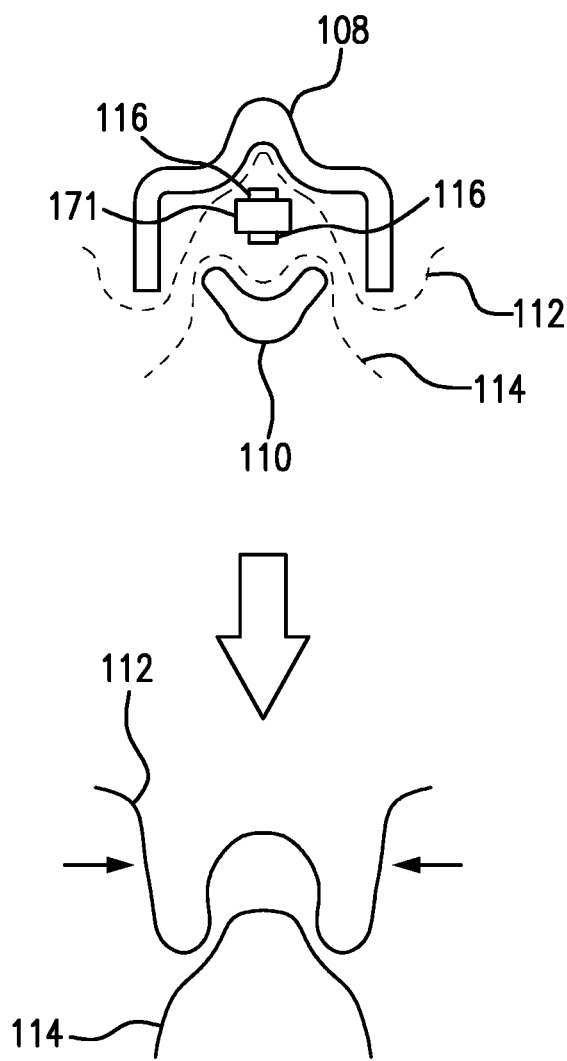

In accordance with yet another aspect of the disclosed subject matter, one or both arms of the fixation device can be provided with first and second wing extensions, and as embodied herein, the first and second wing extensions in end cross-section extend toward the other arm. Furthermore, one arm can be configured, by size and/or shape, to be received between the wing extensions of the other arm. With reference to FIGS. 19-20, each first and second wing extension 162, 163 in end cross-section can extend laterally from the respective body lateral side 158 to define an outer lateral edge as previously discussed, and then can extend generally perpendicularly to the outer lateral edge 166. The fixation device 104 can include a second arm 110 moveably coupled to the central assembly 171, and as embodied herein, the second arm 110 includes a body portion 145 having a first end 140 and a second end 142, the second end 142 being moveable between a closed position and an open position. In the closed position, the at least one arm 108 is sized to surround the second arm 110 on at least three sides of the at least one arm 108 as depicted in end cross-section. In this manner, and as depicted in FIG. 20, the leaflet captured therebetween can be grasped at multiple locations for more secure engagement. This asymmetric arm configuration disclosed herein can increase the tissue contact patch area with a relatively small change to the outer width dimension of the fixation device. The area of tissue captured is wider because the contact patch curves around features in the clip arms. FIGS. 19-20B depict oversized first arms 108 of various sizes, and as embodied herein, each oversized arm is paired with a second arm 110 without wing extensions. For example, the arm shown in FIG. 20A is depicted with a significant overbite, while the arm shown in FIG. 20B is depicted with a more minor overbite. A user can select between designs of various sizes, for example by how much redundant leaflet tissue is observed in a valve being treated. The user can select the size to apply an amount of leaflet tension to stabilize the valve leaflets without inducing leaflet tears.

Figure 21A:
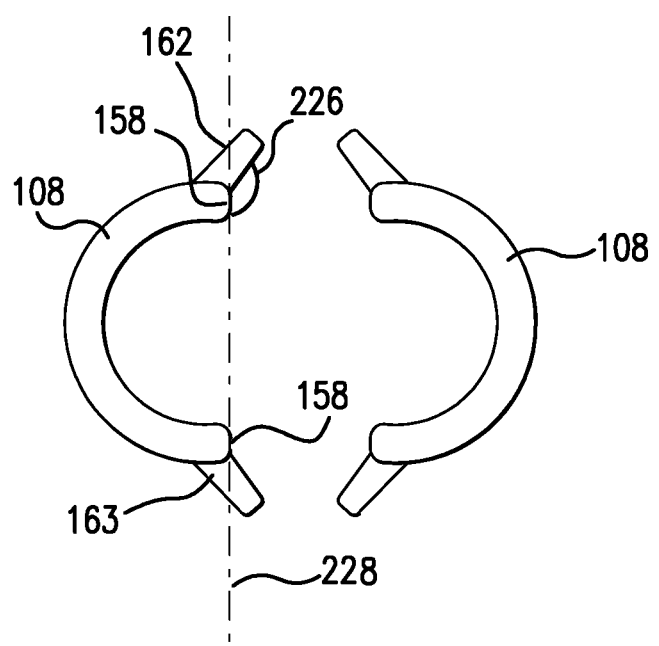
FIG. 21A is a schematic illustrating an end cross-section view of an alternative embodiment of an arm in accordance with the disclosed subject matter.
Figure 21B:
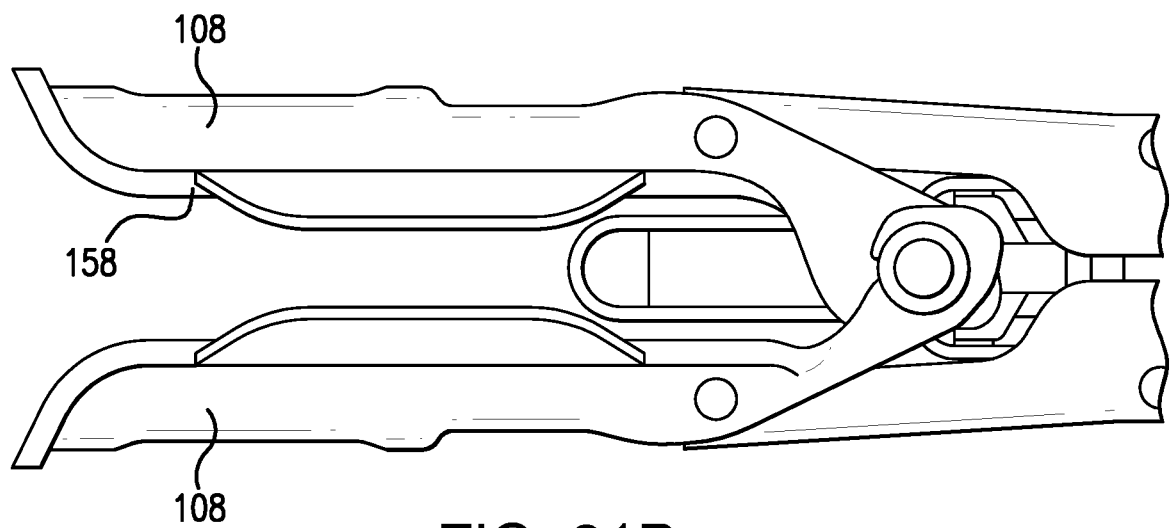
FIG. 21B is a side view of the fixation device of FIG. 1, with the alternative embodiment of the arm of FIG. 21A.

With reference to FIGS. 21A-21B, and in accordance with another aspect of the disclosed subject matter, each first and second wing extension 162, 163 in end cross-section can extend at a wing extension angle 226 defined between the wing extension and a reference axis 228 extending through the opposing body lateral sides 158 of each respective first and second wing extension 162, 163. As embodied herein, the wing extension angle 226 is between 125 and 145 degrees, and in some embodiments, the wing extension angle 226 can be about 135 degrees. Angled wing extensions can allow for an increased contact patch area with a relatively small change to the outer width dimension of the fixation device.

For each embodiment disclosed herein, and with reference again to FIG. 1, the fixation device 104 can further include two link members or legs 168, and as embodied herein, each leg 168 has a first end rotatably joined with one of the arms 108, 110 and a second end rotatably joined with a base 170. The base 170 can be operatively connected with a stud 176 which can be operatively attached to a distal end of a delivery shaft 102. In some embodiments, the stud 176 can be threaded such that the distal end of a delivery shaft 102 can attach to the stud 176 by a screw-type action. Further, the connection point between the stud 176 and the distal end of a delivery shaft 102 can be disposed within the coupling member 174. However, the distal end of a delivery shaft 102 and stud 176 can be operatively connected by any mechanism which is releasable to allow the fixation device 104 to be detached. The stud can be axially extendable and retractable to move the base and therefore the legs 168, which can rotate the arms 108, 110 between closed, open and inverted positions. Immobilization of the stud, such as by a locking mechanism, can hold the legs 168 in place and therefore lock the arms 108, 110 in a desired position. Further details are disclosed in the patents and published applications incorporated by reference herein.

The embodiments illustrated herein are adapted for repair of a heart valve, such as a mitral valve, using an antegrade approach from a patient's left atrium. Prior to a procedure, imaging and various tests can be performed to anticipate and diagnose a patient's individual circumstances and assist a physician in selecting a fixation device having the desired parameters. A physician can select an appropriate fixation device 104 from a kit of fixation devices 104 for fixation of leaflets of a heart valve comprising a plurality of fixation devices 104. As previously discussed, for illustration and not limitation, each fixation device 104 can include a central assembly 171 and at least one arm 108 moveably coupled to the central assembly, and as embodied herein, the at least one arm 108 includes a body portion 160 having a first end 140 and a second end 142, the second end 142 being moveable between a closed position and an open position, and a longitudinal axis 156 defined therebetween. The body portion 145 has opposing body lateral sides 158, each body lateral side 158 extending between the first end 140 and the second end 142, the body portion 145 having a body portion width 160 defined between the opposing body lateral sides 158. Each fixation device 104 in the kit further includes at least one gripping element 116 moveable relative to the at least one arm 108 to capture a native leaflet therebetween. In the kit, the at least one arm 108 can have differing length and width dimensions among the plurality of fixation devices 104.

Figure 17A:
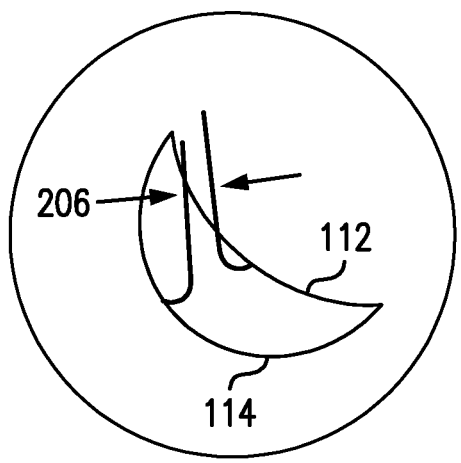
FIGS. 17A-17C are schematic diagrams of various width and length measurements of a heart valve.
Figure 17B:
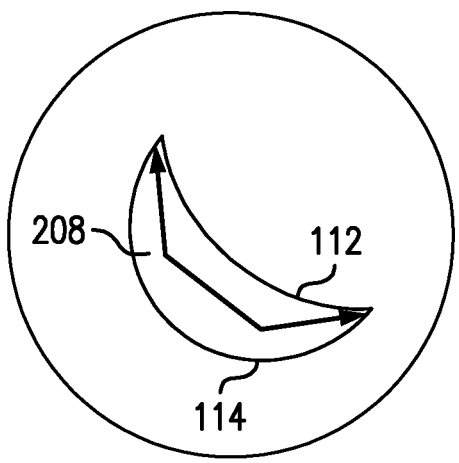
Figure 17C:
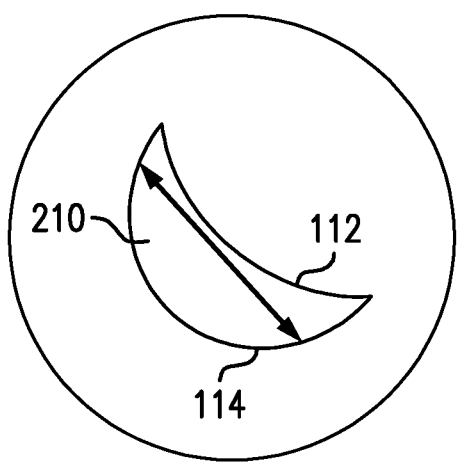

For purpose of illustration and understanding, and not limitation, reference is made to an exemplary procedure using the kit of the disclosed subject matter. Upon evaluation, a physician can select a fixation device having wing extensions, for example if one or more of the following parameters are met. If a patient's regurgitant jet vena contracta width 206, as illustrated in FIG. 17A, is greater than 0.300 inch, the physician can select a fixation device with wing extensions. If a patient's regurgitant area curved length 208, as illustrated in FIG. 17B, is greater than 0.590 inch, the physician can select a fixation device with wing extensions. If a patient's regurgitant area straight length 210, as illustrated in FIG. 17C, is greater than 0.394 inch, the physician can select a fixation device with wing extensions. If a patient's regurgitant orifice area, as assessed by transesophageal echocardiography, is greater than about 0.092 inch squared, the physician can select a fixation device with wing extensions.

The selected fixation device 104 can be introduced in a femoral vein of a patient and advanced through the inferior vena cava into the heart and across a penetration in the interatrial septum. For mitral valve repair, the fixation device 104 can be advanced through the mitral valve from the left atrium to the left ventricle. The arms 108, 110 can be oriented to be perpendicular to a line of coaptation and positioned with the arms 108, 110 contacting the ventricular surface of the valve leaflets, thereby grasping the leaflets. The gripping elements 116, 118 can remain on the atrial side of the valve leaflets with the leaflets disposed between the gripping elements 116, 118 and the arms 108, 110. The fixation device 104 can be manipulated as desired to reposition the device such that the leaflets are properly grasped at a desired location. Repositioning can be performed with the fixation device 104 in the open position. As embodied herein, regurgitation of the valve can also be checked while the fixation device 104 is in the open position. If regurgitation is not satisfactorily reduced, the fixation device 104 can be repositioned and regurgitation checked again until the desired results are achieved.

Once the fixation device 104 has been positioned in a desired location relative to the valve leaflets, the leaflets can then be captured between the gripping elements 116, 118 and the arms 108, 110. As embodied herein, the gripping elements 116, 118 can be lowered toward the arms 108, 110 to dispose the leaflets therebetween. The arms 108, 110 can be closed to an angle selectable by the user and locked to the prevent the arms 108, 110 from moving toward an open position. The fixation device 104 can then be detached from the distal end of the delivery shaft 102. After detachment, the repair of the leaflets or tissue can be observed by non-invasive visualization techniques, such as echocardiography, to ensure the desired outcome. If the repair is not desired, the fixation device 14 can be retrieved. If the repair is satisfactory, the gripper element lines can be disconnected, and the fixation device can be released for implantation.

While the embodiments disclosed herein utilize a push-to-open, pull-to-close mechanism for opening and closing arms it should be understood that other suitable mechanisms can be used, such as a pull-to-open, push-to-close mechanism. A closure bias can be included, for example using a compliant mechanism such as a linear spring, helical spring, or leaf spring. Other actuation elements can be used for deployment of the gripper elements.

Figure 18:
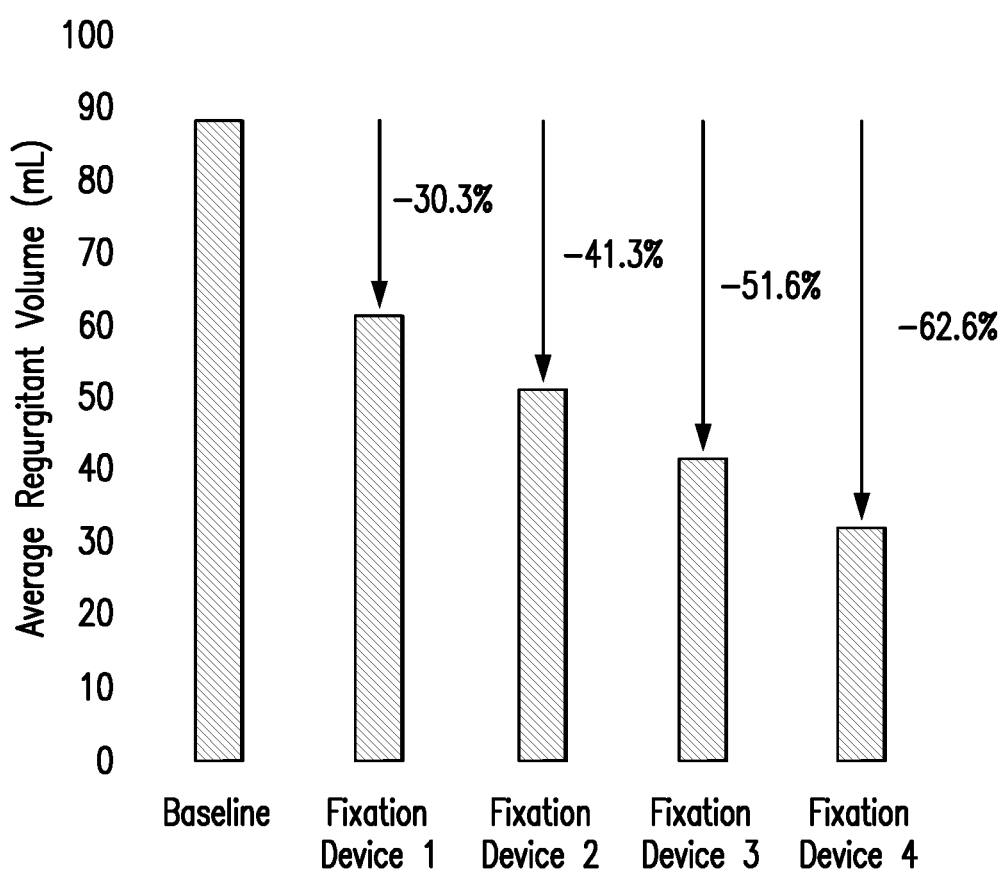
FIG. 18 is a diagram illustrating regurgitant volume versus fixation device size.

With reference now to FIG. 18, exemplary results are provided for average regurgitant volume in mL as a function of devices with varied arm sizes. In this example, a simulated left ventricle systolic pressure of 100 mmHg and a silicone mitral valve having clinically relevant moderate to severe regurgitation were induced. Regurgitant flow volume data was obtained by measuring backward flow across the valve without a fixation device, for a baseline, and with each of 4 devices of varying sizes. Fixation Device 1 had arms each having an arm length 204 of about 0.422 inch and a standard arm width of about 0.135 inch. Fixation Device 2 was sized with arms each having an arm length 204 of about 0.522 inch and a standard arm width (e.g., without wing extensions) of about 0.135 inch. Fixation Device 3 was sized with arms each having an arm length 204 of about 0.422 inch and wing extensions, as disclosed herein, with a width of about 0.203 inch. Fixation Device 4 was sized with arms each having an arm length 204 of about 0.522 inch and wing extensions, as disclosed herein, with a width of about 0.203 inch. The average regurgitant volume for the baseline was about 88 mL, for Fixation Device 1 was 62 mL, for Fixation Device 2 was 53 mL, for Fixation Device 3 was 42 mL, and for Fixation Device 4 was 32 mL. Thus, average regurgitant volume was reduced by about an additional 21.3% with a fixation device of the disclosed subject matter, i.e., with wing extensions.

While the disclosed subject matter is described herein in terms of certain preferred embodiments for purpose of illustration and not limitation, those skilled in the art will recognize that various modifications and improvements can be made to the disclosed subject matter without departing from the scope thereof. Moreover, although individual features of one embodiment of the disclosed subject matter can be discussed herein or shown in the drawings of one embodiment and not in other embodiments, it should be readily apparent that individual features of one embodiment can be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A fixation device for fixation of leaflets of a heart valve comprising:
   a central assembly;
   at least one arm moveably coupled to the central assembly, the at least one arm comprising:
      a body portion having a first end and a second end and a longitudinal axis defined therebetween, the second end being moveable between a closed position and an open position, the body portion having opposing body lateral sides, each body lateral side extending between the first end and the second end, the body portion having a body portion width defined between the opposing body lateral sides,
      first and second nondeformable wing extensions, each wing extension extending laterally from a respective lateral side, each wing extension having a lateral outer edge, wherein a maximum arm width is defined between the outer lateral edge of the first wing extension and the outer lateral edge of the second wing extension;
         wherein the first and second wing extensions each have a first end edge and a second end edge, wherein the first end edge extends between the respective body lateral side and the outer lateral edge and is located proximate the first end of the body portion, and the second end edge extends between the respective body lateral side and the outer lateral edge and is located proximate the second end of the body portion, and
         wherein the first end edge has a first end fillet at an intersection with the respective body lateral side, wherein the first end fillet has a radius of curvature between one and eleven times a thickness of the arm; and
   at least one gripping element moveable relative to the at least one arm to capture a native leaflet therebetween.

2. The device of claim 1, wherein the maximum arm width is between about 1.40 and 1.60 times the body portion width.

3. The device of claim 1, wherein the maximum arm width is about 1.50 times the body portion width.

4. The device of claim 1, wherein the first end edge extends from the body lateral side at a first end angle defined between the first end edge and the longitudinal axis, wherein the first end angle is between 30 and 60 degrees.

5. The device of claim 4, wherein the first end angle is 45 degrees.

6. The device of claim 4, wherein a first end lead dimension is defined along the body portion by a distance between the first end of the body portion and an intersection of the first end edge and the respective body lateral side, wherein the first end lead dimension is between about 0.15 inch and 0.25 inch.

7. The device of claim 6, wherein the first end lead dimension is 0.19 inch.

8. The device of claim 4, wherein a second end lead dimension is defined along the body portion by a distance between the second end of the body portion and an intersection of the second end edge and the respective body lateral side, wherein the second end lead dimension is between about 0.05 inch and 0.15 inch.

9. The device of claim 8, wherein the second end lead dimension is 0.09 inch.

10. The device of claim 4, wherein a first end lead dimension is defined along the body portion by a distance between the first end of the body portion and an intersection of the first end edge and the respective body lateral side, and a second end lead dimension is defined along the body portion by a distance between the second end of the body portion and an intersection of the second end edge and the respective body lateral side, and the second end lead dimension is less than one third of the first end lead dimension.

11. The device of claim 1, wherein the second end edge extends from the respective body lateral side at a second end angle defined between the second end edge and the longitudinal axis, wherein the second end angle is between 30 and 60 degrees.

12. The device of claim 11, wherein the second end angle is 45 degrees.

13. The device of claim 1, wherein the arm has a thickness of about 0.015 inch.

14. The device of claim 1, wherein the first end fillet has a radius of curvature between about 0.02 inch and 0.165 inch.

15. The device of claim 1, wherein the first end fillet has a radius of curvature of 0.12 inch.

16. The device of claim 1, wherein the first end fillet has a radius of curvature eight times the thickness of the arm.

17. The device of claim 1, wherein a second end edge extends from the second end of the body portion at a second end angle defined between the second end edge and the longitudinal axis, wherein the second end angle is between 30 and 60 degrees.

18. The device of claim 1, wherein the first end edge, lateral outer edge, and second end edge form a continuous complex curve.

19. The device of claim 1, wherein the at least one arm further has a recessed trough along the longitudinal axis, the trough having a trough width sized greater than a width of the at least one gripping element.

20. The device of claim 19, wherein the trough width increases from the first end of the body portion to the second end of the body portion.

21. The device of claim 1, wherein the first and second wing extensions and the body portion are a single piece.

22. The device of claim 1, wherein each first and second wing extension in end cross-section extends laterally from the respective body lateral side and then extends perpendicularly to the outer lateral edge.

23. The device of claim 22, wherein the fixation device comprises a second arm moveably coupled to the central assembly, the second arm comprising a body portion having a first end and a second end, the second end being moveable between a closed position and an open position, wherein in the closed position, the at least one arm is sized to surround the second arm on at least three sides of the at least one arm.

24. The device of claim 1, wherein each first and second wing extension in end cross-section extends at a wing extension angle defined between the wing extension and a reference axis extending through the opposing body lateral sides of each respective first and second wing extension, wherein the wing extension angle is between 125 and 145 degrees.

25. The device of claim 1, wherein the wing extension angle is about 135 degrees.

26. The device of claim 1, wherein the at least one gripping element has at least one friction element along a length thereof.

27. The device of claim 26, wherein the at least one gripping element has a plurality of friction elements along the length thereof, wherein when the at least one gripping element is located proximate the at least one arm the plurality of friction elements are disposed along a length defined between the intersection of the first end edge and the respective body lateral side, and the intersection of the second end edge and the respective body lateral side.

28. The device of claim 1, wherein the fixation device further comprises:
a second arm moveably coupled to the central assembly, the second arm comprising a second body portion having a first end and a second end, the second end being moveable between a closed position and an open position; and
a second gripping element moveable relative to the second arm to capture a native leaflet therebetween.

29. A fixation device for fixation of leaflets of a heart valve comprising:
a central assembly;
at least one arm moveably coupled to the central assembly, the at least one arm comprising:
a body portion having a first end and a second end and a longitudinal axis defined therebetween, the second end being moveable between a closed position and an open position, the body portion having opposing body lateral sides, each body lateral side extending between the first end and the second end, the body portion having a body portion width defined between the opposing body lateral sides,
first and second nondeformable wing extensions, each wing extension extending laterally from a respective lateral side, each wing extension having a lateral outer edge, wherein a maximum arm width is defined between the outer lateral edge of the first wing extension and the outer lateral edge of the second wing extension;
wherein the first and second wing extensions each have a first end edge and a second end edge, wherein the first end edge extends between the respective body lateral side and the outer lateral edge and is located proximate the first end of the body portion, and the second end edge extends between the respective body lateral side and the outer lateral edge and is located proximate the second end of the body portion, and
wherein the second end edge has a second end fillet at an intersection with the body lateral side, wherein the second end fillet has a radius of curvature between one and eleven times a thickness of the arm; and
at least one gripping element moveable relative to the at least one arm to capture a native leaflet therebetween.

30. The device of claim 29, wherein the arms each have a thickness of about 0.015 inch.

31. The device of claim 29, wherein the second end fillet has a radius of curvature between about 0.02 inch and 0.165 inch.

32. The device of claim 29, wherein the second end fillet has a radius of curvature of 0.12 inch.

33. The device of claim 29, wherein the second end fillet has a radius of curvature eight times the thickness of the arm.

34. A fixation device for fixation of leaflets of a heart valve comprising:
 a central assembly;
 at least one arm moveably coupled to the central assembly, the at least one arm comprising:
  a body portion having a first end and a second end and a longitudinal axis defined therebetween, the second end being moveable between a closed position and an open position, the body portion having opposing body lateral sides, each body lateral side extending between the first end and the second end, the body portion having a body portion width defined between the opposing body lateral sides,
  first and second nondeformable wing extensions, each wing extension extending laterally from a respective lateral side, each wing extension having a lateral outer edge, wherein a maximum arm width is defined between the outer lateral edge of the first wing extension and the outer lateral edge of the second wing extension;
  wherein the first and second wing extensions each have a first end edge and a second end edge, wherein the first end edge extends between the respective body lateral side and the outer lateral edge and is located proximate the first end of the body portion, and the second end edge extends between the respective body lateral side and the outer lateral edge and is located proximate the second end of the body portion, and
  wherein the first end edge has a first end round at an intersection with the outer lateral edge, wherein the first end round has a radius of curvature between one and eleven times a thickness of the arm; and
 at least one gripping element moveable relative to the at least one arm to capture a native leaflet therebetween.

35. The device of claim 34, wherein the arms each have a thickness of about 0.015 inch.

36. The device of claim 34, wherein the first end round has a radius of curvature between about 0.02 inch and 0.165 inch.

37. The device of claim 34, wherein the first end round has a radius of curvature of 0.12 inch.

38. The device of claim 34, wherein the first end round has a radius of curvature eight times the thickness of the arm.

39. A fixation device for fixation of leaflets of a heart valve comprising:
 a central assembly;
 at least one arm moveably coupled to the central assembly, the at least one arm comprising:
  a body portion having a first end and a second end and a longitudinal axis defined therebetween, the second end being moveable between a closed position and an open position, the body portion having opposing body lateral sides, each body lateral side extending between the first end and the second end, the body portion having a body portion width defined between the opposing body lateral sides,
  first and second nondeformable wing extensions, each wing extension extending laterally from a respective lateral side, each wing extension having a lateral outer edge, wherein a maximum arm width is defined between the outer lateral edge of the first wing extension and the outer lateral edge of the second wing extension;
  wherein the first and second wing extensions each have a first end edge and a second end edge, wherein the first end edge extends between the respective body lateral side and the outer lateral edge and is located proximate the first end of the body portion, and the second end edge extends between the respective body lateral side and the outer lateral edge and is located proximate the second end of the body portion, and
  wherein the second end edge has a second end round at an intersection with the outer lateral edge, wherein the second end round has a radius of curvature between one and eleven times a thickness of the arm; and
 at least one gripping element moveable relative to the at least one arm to capture a native leaflet therebetween.

40. The device of claim 39, wherein the arms each have a thickness of about 0.015 inch.

41. The device of claim 39, wherein the second end round has a radius of curvature between about 0.02 inch and 0.165 inch.

42. The device of claim 39, wherein the second end round has a radius of curvature of 0.12 inch.

43. The device of claim 39, wherein the second end round has a radius of curvature eight times the thickness of the arm.

44. A kit of fixation devices for fixation of leaflets of a heart valve comprising:
 a plurality of fixation devices, each fixation device comprising:
  a central assembly;
  at least one arm moveably coupled to the central assembly, the at least one arm, comprising:
   a body portion having a first end and a second end, the second end being moveable between a closed position and an open position, and a longitudinal axis defined therebetween, the body portion having opposing body lateral sides, each body lateral side extending between the first end and the second end, the body portion having a body portion width defined between the opposing body lateral sides,
   wherein the first and second wing extensions each have a first end edge and a second end edge, wherein the first end edge extends between the respective body lateral side and the outer lateral edge and is located proximate the first end of the body portion, and the second end edge extends between the respective body lateral side and the outer lateral edge and is located proximate the second end of the body portion, and
   wherein the first end edge has a first end fillet at an intersection with the respective body lateral side, wherein the first end fillet has a radius of curvature between one and eleven times a thickness of the arm, and
  at least one gripping element moveable relative to the at least one arm to capture a native leaflet therebetween, and
 wherein the at least one arm has differing length and width dimensions between the plurality of fixation devices.

* * * * *